United States Patent
Terzian et al.

(10) Patent No.: US 12,029,732 B2
(45) Date of Patent: Jul. 9, 2024

(54) TREATMENT OF VASCULAR AND LYMPHATIC DISEASE

(71) Applicant: THE REGENTS OF THE UNIVERSITY OF COLORADO, A BODY CORPORATE, Denver, CO (US)

(72) Inventors: Tamara Terzian, Aurora, CO (US); Neil Box, Aurora, CO (US)

(73) Assignee: The Regents of the University of Colorado, A Body Corporate, Denver, CO (US)

(*) Notice: Subject to any disclaimer, the term of this patent is extended or adjusted under 35 U.S.C. 154(b) by 74 days.

(21) Appl. No.: 17/604,858

(22) PCT Filed: Apr. 20, 2020

(86) PCT No.: PCT/US2020/029015
§ 371 (c)(1),
(2) Date: Oct. 19, 2021

(87) PCT Pub. No.: WO2020/215091
PCT Pub. Date: Oct. 22, 2020

(65) Prior Publication Data
US 2022/0218674 A1    Jul. 14, 2022

Related U.S. Application Data

(60) Provisional application No. 62/990,932, filed on Mar. 17, 2020, provisional application No. 62/836,535, filed on Apr. 19, 2019.

(51) Int. Cl.
*A61K 31/428* (2006.01)
*A61K 31/429* (2006.01)
*A61P 7/10* (2006.01)

(52) U.S. Cl.
CPC .......... *A61K 31/428* (2013.01); *A61K 31/429* (2013.01); *A61P 7/10* (2018.01)

(58) Field of Classification Search
CPC ........ A61K 31/428; A61K 31/429; A61P 7/10
See application file for complete search history.

(56) References Cited

U.S. PATENT DOCUMENTS

| 2003/0026831 A1 | 2/2003 | Lakkaraju et al. |
| 2015/0224088 A1* | 8/2015 | Sarkar .................. A61K 31/428 514/35 |
| 2020/0085925 A1 | 3/2020 | Burkart et al. |

FOREIGN PATENT DOCUMENTS

| WO | 00/75163 A1 | 12/2000 |
| WO | WO-0075163 A1 * | 12/2000 ......... A61K 38/1858 |
| WO | 2016/185457 A1 | 11/2016 |

OTHER PUBLICATIONS

International Search Report and Written Opinion issued in International Application No. PCT/US2020/029015 dated Sep. 30, 2020 (10 pages).
Box et al., "Targeting p53 in melanoma", Pigment Cell Melanoma Res., 2014, 27(1): 8-10 (5 pages).

* cited by examiner

*Primary Examiner* — Michael B. Pallay
(74) *Attorney, Agent, or Firm* — Dorsey & Whitney LLP

(57) ABSTRACT

Disclosed herein are compositions, methods, and systems useful in the prevention, management, or treatment of various conditions associated the lymphatic vasculature, including, but not limited to lymphedema. The disclosed methods and compositions are useful in reducing the activity of p53 in a subject at risk for or suffering from a disease or condition associated with lymphatic vasculature, including adults, children, infants, and embryos. Reduction in p53 activity may be achieve through reduction in one or more of p53 gene expression, p53 transcriptional activity, p53 DNA-binding affinity, etc. In many embodiments, the disease or condition is lymphedema, for example lymphedema associated with Milroy's disease, Klippel-Trenaunay and Cloves Syndromes. In many embodiments, treatment may involve administering a compound or pharmaceutically acceptable salt thereof to a subject in need thereof, exemplary compounds include, anti-p53 compounds, PFT, and PFT-β.

18 Claims, 27 Drawing Sheets

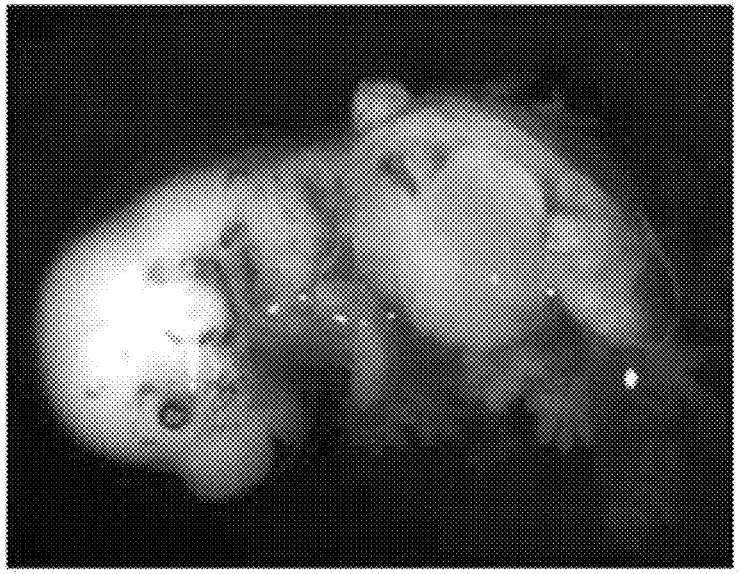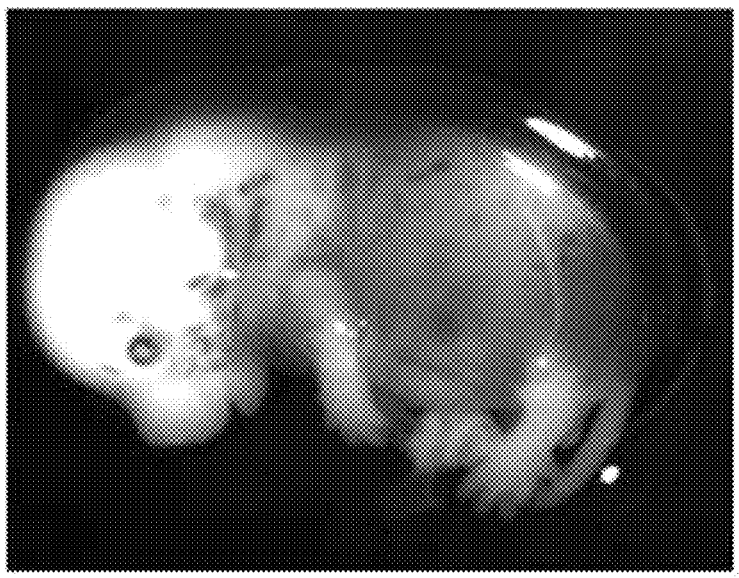
FIG. 4B a
| Crosses | Genotypes | Progeny observed (expected) * |
|---|---|---|
| Rpl27a^(sooty/+) x Mdm2^(+/-);p53^(+/-) | Mdm2^(+/-);p53^(+/-) | 20 (22) |
| | Rpl27a^(sooty/+);Mdm2^(+/-);p53^(+/-) | 24 (22) |
| Rpl27a^(sooty/+) x Mdm4^(+/-);p53^(+/-) | Mdm4^(+/-);p53^(+/-) | 29 (27) |
| | Rpl27a^(sooty/+);Mdm4^(+/-);p53^(+/-) | 25 (27) |
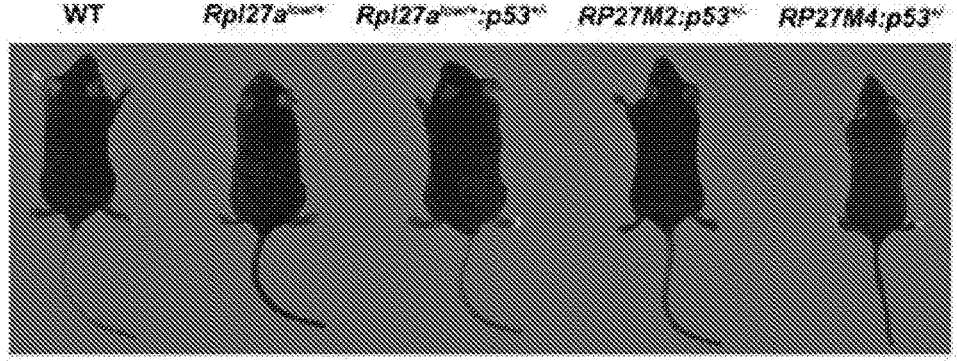
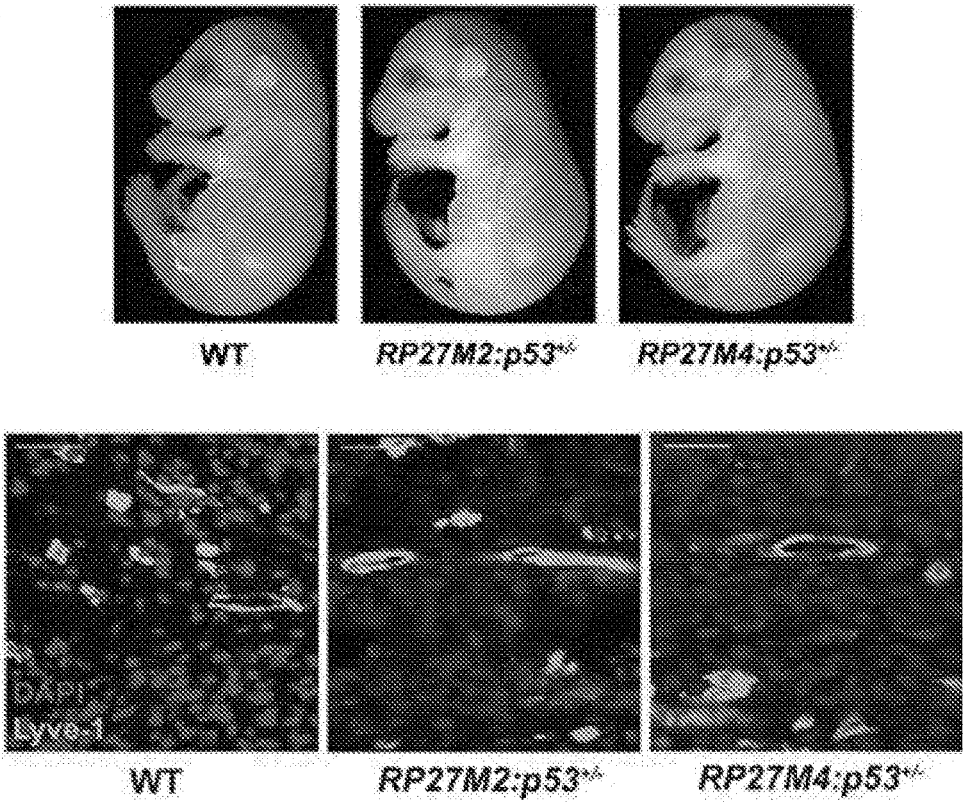
FIG. 8 a
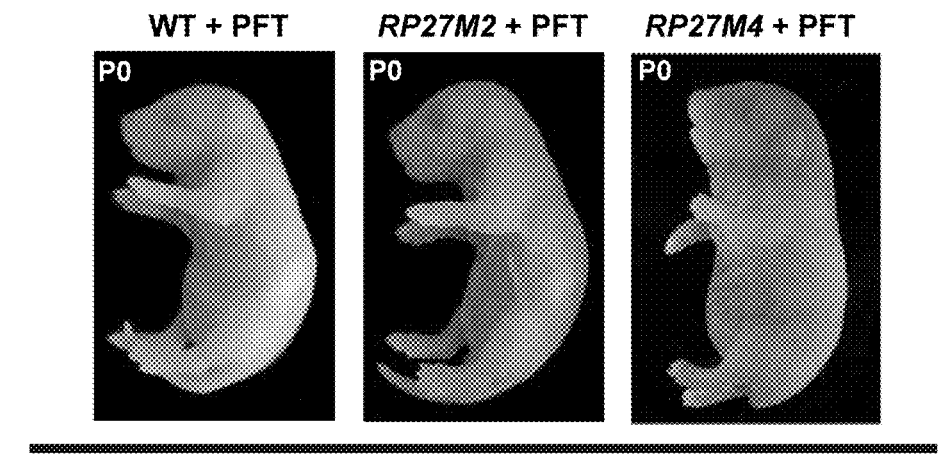
b
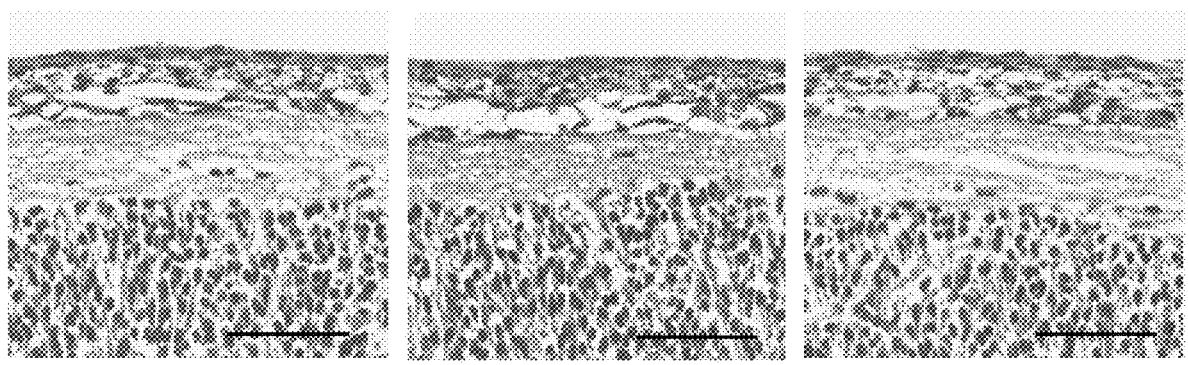
FIG. 9A

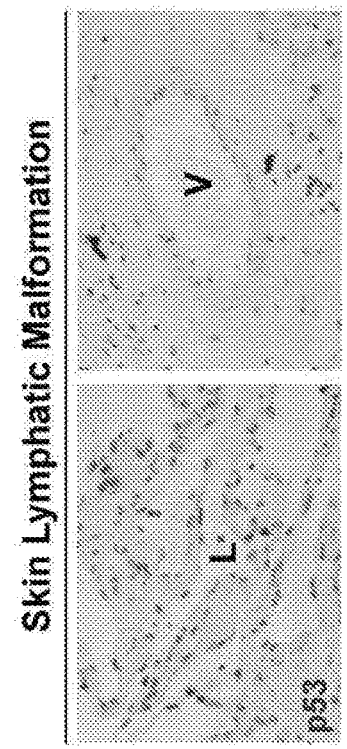

| Sample # | Diagnosis | Age | Sex | Tissue/Region | p53 |
|---|---|---|---|---|---|
| 1 | Microcystic Lymphatic Malformation | 11 y/o | M | Dermis/Buttock | ++ |
| 2 | Generalized Lymphatic Anomaly | 21 y/o | F | Dermis/Perineum | ~ |
| 3 | Macrocystic Lymphatic Malformation | 10 y/o | M | Mesentery | ++ |
| 4 | Macrocystic Lymphatic Malformation | 2 y/o | M | Omental fat pad | ++ |
| 5 | CLOVES | 5 y/o | F | Dermis/Buttock | ++ |
| 6 | Macrocystic Lymphatic Malformation | 13 y/o | F | Dermis/Perineum | ~ |
| 7 | Kippel Trenaunay | 2 m/o | F | Dermis/Leg | ++ |
| 8 | Lymphatic Malformation | 8 y/o | F | Dermis | ++ |

FIG. 12 a  Edema Scoring
WT - 0　　　　Mild - 1　　　　Moderate - 2　　　　Severe - 3
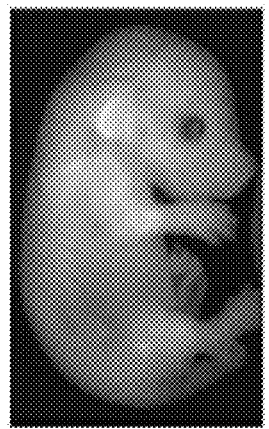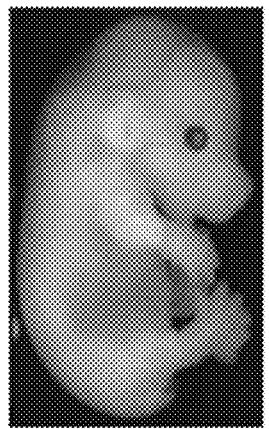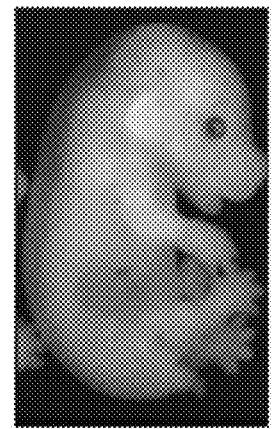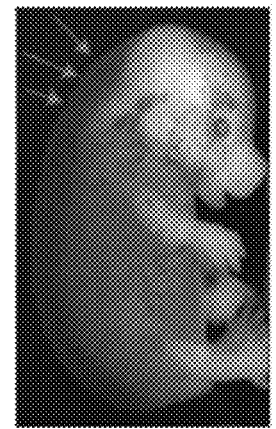
Hemorrhage Scoring
WT - 0　　　　Mild - 1　　　　Moderate - 2　　　　Severe - 3
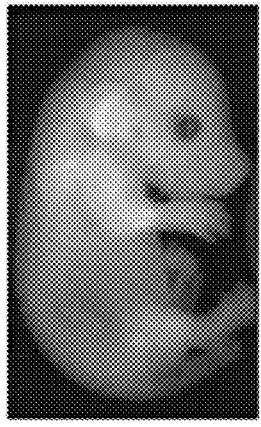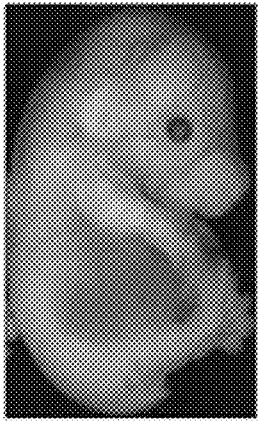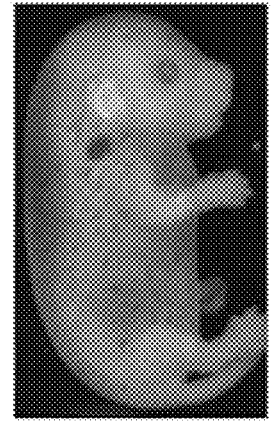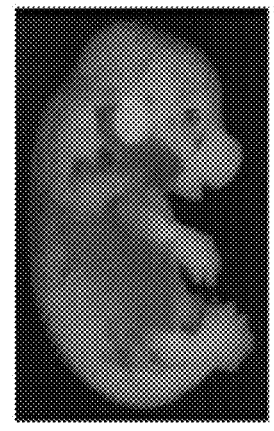
FIG. 14A Table 1

| Gestational Age | N | WT (%) Observed | WT (%) Expected | Rpl27a+/- (%) Observed | Rpl27a+/- (%) Expected | Mdm2+/- (%) Observed | Mdm2+/- (%) Expected | Rpl27a+/-;Mdm2+/- (%) Observed | Rpl27a+/-;Mdm2+/- (%) Expected |
|---|---|---|---|---|---|---|---|---|---|
| 11.5 | 24 | 7 (29) | 6 (25) | 8 (33) | 6 (25) | 6 (25) | 6 (25) | 3 (13) | 6 (25) |
| 12.5 | 31 | 1 (6) | 7.75 (25) | 12 (39) | 7.75 (25) | 10 (32) | 7.75 (25) | 8 (26) | 7.75 (25) |
| 13.5 | 89 | 34 (38) | 22.25 (25) | 19 (21) | 22.25 (25) | 14 (16) | 22.25 (25) | 22 (25) | 22.25 (25) |
| 14.5 | 147 | 37 (25) | 36.75 (25) | 39 (27) | 36.75 (25) | 34 (23) | 36.75 (25) | 37 (25) | 36.75 (25) |
| 15.5 | 80 | 18 (23) | 20 (25) | 24 (30) | 20 (25) | 17 (22) | 20 (25) | 21 (25) | 20 (25) |
| 16.5 | 54 | 15 (28) | 13.5 (25) | 15 (28) | 13.5 (25) | 12 (22) | 13.5 (25) | 12 (22) | 13.5 (25) |
| 18.5 | 12 | 1 (8) | 3 (25) | 5 (42) | 3 (25) | 6 (50) | 3 (25) | 0 (0) | 3 (25) |
| P28 | 100 | 34 (34) | 25 (25) | 32 (32) | 25 (25) | 34 (34) | 25 (25) | 0 (0) | 25 (25) |

Fig 18

Table 2

| Gestational Age | N | WT (%) Observed | WT (%) Expected | Rpl27a^low/+ (%) Observed | Rpl27a^low/+ (%) Expected | Mdm4^+/- (%) Observed | Mdm4^+/- (%) Expected | Rpl27a^low/+;Mdm4^+/- (%) Observed | Rpl27a^low/+;Mdm4^+/- (%) Expected |
|---|---|---|---|---|---|---|---|---|---|
| 11.5 | 18 | 3 (17) | 4.5 (25) | 6 (33) | 4.5 (25) | 4 (22) | 4.5 (25) | 5 (28) | 4.5 (25) |
| 12.5 | 54 | 18 (33) | 13.5 (25) | 9 (17) | 13.5 (25) | 14 (26) | 13.5 (25) | 13 (24) | 13.5 (25) |
| 13.5 | 143 | 40 (28) | 35.75 (25) | 32 (22) | 35.75 (25) | 41 (29) | 35.75 (25) | 30 (21) | 35.75 (25) |
| 14.5 | 172 | 48 (28) | 43 (25) | 36 (21) | 43 (25) | 46 (27) | 43 (25) | 42 (24) | 43 (25) |
| 15.5 | 83 | 22 (27) | 20.75 (25) | 24 (29) | 20.75 (25) | 22 (27) | 20.75 (25) | 15 (17) | 20.75 (25) |
| 16.5 | 30 | 7 (23) | 7.5 (25) | 9 (30) | 7.5 (25) | 9 (30) | 7.5 (25) | 5 (17) | 7.5 (25) |
| 18.5 | 9 | 6 (66) | 2.25 (25) | 3 (34) | 2.25 (25) | 0 (0) | 2.25 (25) | 0 (0) | 2.25 (25) |
| P28 | 46 | 16 (33) | 12 (25) | 16 (31) | 12 (25) | 17 (36) | 12 (25) | 0 (0) | 12 (25) |

Table 4

| Mouse ID | Test Group | Body Weight | Liver Weight | Kidney Weight | Liver/Body | Kidney/Body |
|---|---|---|---|---|---|---|
| | *reference values* | | | | | |
| CSD 472 | control/untreated | 27.00g | 1.52g | 0.34g | 0.0563 | 0.0126 |
| CSD 478 | cyclic PFT | 24.65g | 0.53g | 0.30g | 0.0215 | 0.0122 |
| CSM 515 | cyclic PFT | 20.85 | 1.5 | 0.25 | 0.072 | 0.0120 |
| CSD 463 | PFT | 29.63g | 1.72g | 0.34g | 0.0580 | 0.0115 |
| CSM 459 | PFT | 28.44 | 2.09 | 0.31 | 0.073 | 0.0109 |
| CSM 516 | PFT | 22.87 | 1.54 | 0.23 | 0.067 | 0.0101 |

| WBC | RBC | HGB | HCT | MCV | MCH | MCHC | LYM | MONO |
|---|---|---|---|---|---|---|---|---|
| 2.6 - 3.9 | 7 - 11.5 | 10.9 - 18.0 | 37 - 58 | 42 - 55 | 13 - 16 | 26 - 35 | 2.32 - 6.71 | 0.3 - .36 |
| 2.2 | 7.45 | 13.4 | 44.3 | 59.5 | 18 | 30.3 | 1.5 | 0.2 |
| 2.1 | 8.34 | 13.3 | 45.3 | 54.3 | 15.9 | 29.4 | 1.5 | 0.1 |
| 2.7 | 7.85 | 12.8 | 38.9 | 49.5 | 16.3 | 32.8 | 2.2 | 0.2 |
| 2.5 | 8.12 | 13.5 | 38.7 | 47.7 | 16.7 | 35 | 1.7 | 0.2 |
| 2.2 | 7.49 | 11.7 | 35.4 | 47.3 | 15.6 | 33 | 1.8 | 0.2 |
| 2.1 | 7.24 | 11.5 | 35.9 | 49.7 | 15.9 | 32.1 | 0.4 | 0.2 |

| GRAN | LYM % | MONO % | GRAN % | RDWa | RDW % | MPV |
|---|---|---|---|---|---|---|
| | 70 - 86 | 2.0 - 7.0 | | | | |
| 0.5 | 67.5 | 8.9 | 23.6 | 44.6 | 21.7 | 9.7 |
| 0.5 | 68.7 | 6.4 | 24.9 | 41.9 | 23.1 | **** |
| 0.3 | 82.4 | 5.4 | 12.2 | 38.9 | 25.2 | **** |
| 0.6 | 66.2 | 8.7 | 25.1 | 36.8 | 25.3 | 6.3 |
| 0.2 | 83.9 | 4.7 | 11.4 | 36.4 | 25.2 | 6.2 |
| 0 | 81.1 | 4.4 | 14.5 | 38.5 | 24.8 | **** |

Fig. 21

TREATMENT OF VASCULAR AND LYMPHATIC DISEASE

CROSS REFERENCE TO RELATED APPLICATIONS

The present application is a national stage application under 35 U.S.C. § 371 of International Application No. PCT/US2020/029015 filed Apr. 20, 2020, which claims the benefit of priority to U.S. Provisional Patent Application No. 62/990,932, entitled "Treatment of Vascular and Lymphatic Disease," filed Mar. 17, 2020, and U.S. Provisional Patent Application No. 62/836,535, entitled "Treatment of Vascular and Lymphatic Disease," filed Apr. 19, 2019, the entireties of all of which are hereby incorporated by reference herein for all purposes.

GOVERNMENT LICENSE RIGHTS

This invention was made with Government support under K01 AR 063203 awarded by the National Institutes of Health. The Government has certain rights in the invention.

FIELD

The disclosed processes, methods, and systems are directed to treating patients suffering from or at risk of developing a disease or condition associated with the lymphatic vasculature, for example lymphedema.

BACKGROUND

Tumor protein p53, or p53, is found in various organisms. The gene is referred to as TP53 in humans and Trp53 in mice. The human TP53 gene encodes at least 15 protein isoforms, ranging in size from 3.5 to 43.7 kDa, all of which are referred to as the p53 isoforms. TP53 is a frequently mutated gene in human cancer, because p53 plays a role in preventing cancer formation and progression. P53 is a transcription factor that acts as a sensor of genomic integrity and a major tumor suppressor. It has been shown to be activated by many types of cellular stressors such as ribosomal stress, DNA damage and oncogene activation. Active p53 can induce multiple important cellular programs including: apoptosis, cell cycle arrest and senescence.

To avoid deleterious effects that elevated p53 may have on healthy cells, p53 is tightly regulated by its main inhibitors Mdm2 and Mdm4. For example, p53 is maintained at very low physiological levels during embryogenesis. Indeed, homozygous deletion of Mdm2 or Mdm4 is embryonic lethal in mice due to aberrantly high levels of p53 resulting in apoptosis or cell cycle arrest, respectively. On the other hand, mice lacking one allele of Mdm2 or Mdm4 alleles are normal, survive to adulthood, and reproduce normally, despite an endogenously active p53. Nevertheless, these haploinsufficient mice show increased p53 activity characterized by augmented sensitivity to DNA damage (gamma IR), decreased transformation potential and tumorigenesis (Terzian T., et al. MCB 2007 and Mendrysa S., et al. 2003).

Applicants and others have observed that haploinsufficiency of some ribosomal protein genes such as Rpl27a lead to elevated p53 levels, in particular in developing tissues such as skin, cerebellum and bone marrow. Interestingly, Rpl27a haploinsufficient mice phenotypically mimic other models with high p53, including bone marrow hypoplasia, cerebellar ataxia and hyperpigmentation (Terzian T., et al. 2011).

Lymphedema is an incurable, disfiguring, and often debilitating disease that develops due to abnormalities in the formation and/or function of the lymphatic system, which results in the accumulation of protein-rich fluid (lymph) in the interstitial space, leading to swelling of small areas of tissue or the entire body. Patients suffering from lymphedema may struggle with self-esteem, psychological pain, and low quality of life. Left untreated, lymphedema can lead to chronic and disabling infections and inflammation.

SUMMARY

Applicants disclose herein a link between p53 and lymphedema, and show that down-regulation of p53 may be useful in the prevention, management, or treatment of various conditions associated the lymphatic vasculature, including, but not limited to lymphedema.

Herein are described compositions and methods useful in treating a subject at risk of developing, or suffering from, a disease or condition associated with lymphedema. For example, disclosed herein are methods of treating a subject at risk for developing a disease or condition associated with the lymphatic vasculature, the method comprising the steps of reducing the activity of p53 in a subject at risk for or suffering from a disease or condition associated with lymphatic vasculature, wherein the disease or condition may be lymphedema, for example lymphedema associated with Milroy's disease, Klippel-Trenaunay and Cloves Syndromes. In many embodiments the reducing step may involve administering a compound or pharmaceutically acceptable salt thereof to the subject, such as an anti-p53 compound, for example 2-[2-Imino-4,5,6,7-tetrahydrobenzothiazol-3-yl]-1-p-tolylethanone, cyclic pifithrin-α hydrobromide, or pharmaceutically acceptable forms (such as a salt) thereof to the patient. In many embodiments the administration may be systemic, such as by intravenous injection or infusion. In some embodiments, the subject may be a human adult, child, infant, or embryo.

Also disclosed are uses of 2-[2-Imino-4,5,6,7-tetrahydrobenzothiazol-3-yl]-1-p-tolylethanone, cyclic pifithrin-α hydrobromide, or pharmaceutically acceptable forms thereof in the manufacture of a medicament for the prevention or treatment of a disease or condition associated with the lymphatic vasculature, such as lymphedema, for example lymphedema associated with Milroy's disease, Klippel-Trenaunay and Cloves Syndromes. In many embodiments the medicament may be for systemic administration, such as by intravenous injection or infusion. In some embodiments, the medicament may be administered to a human adult, child, infant, or embryo.

Also disclosed are methods of promoting development of a lymphatic vessel in a subject in need thereof, the method comprising the steps of reducing the activity of p53 in, at, or near a lymphatic vessel cell, wherein the subject is at risk for developing, or suffers from lymphedema, such as lymphedema associated with Milroy's disease, Klippel-Trenaunay Syndrome, and Cloves Syndrome. In many embodiments the reducing step may involve administering a compound or pharmaceutically acceptable salt thereof to the subject, such as an anti-p53 compound, for example 2-[2-Imino-4,5,6,7-tetrahydrobenzothiazol-3-yl]-1-p-tolylethanone, cyclic pifithrin-α hydrobromide, or pharmaceutically acceptable forms thereof to the patient. In many embodiments the administration may be systemic, such as by intravenous injection or infusion. In some embodiments, the subject may be a human adult, child, infant, or embryo.

Also disclosed are compositions for the prevention or treatment of a disease or condition associated with the lymphatic vasculature, comprising 2-[2-Imino-4,5,6,7-tetrahydrobenzothiazol-3-yl]-1-p-tolylethanone, cyclic pifithrin-α hydrobromide, or pharmaceutical forms (such as a salt) thereof, and a carrier. The disease or condition may be lymphedema, such as lymphedema associated with Milroy's disease, Klippel-Trenaunay Syndrome, and Cloves Syndrome. In many embodiments the composition may be administered systemically, such as by intravenous injection or infusion. In some embodiments, the composition may be administered to a subject that is a human adult, child, infant, or embryo.

BRIEF DESCRIPTION OF THE DRAWINGS

FIGS. 4A and 4B show results indicating major organs in mutant embryos are normal. FIG. 4A Panel a shows H&E staining of E15.5 embryos. FIG. 4B Panel b shows images of a mutant embryo before and after skin removal showing a clear view of the liver and no internal hemorrhaging.

FIG. 5A Panel a shows IF for lymphatic marker Lyve-1 shows distended lymphatic vessels in mutants compared to WT. FIG. 5A Panel b shows Confocal images of whole-mount skin stained for lymphatic markers Vegfr-3 and Prox-1 and general endothelial marker PECAM-1. FIG. 5B Panel c shows a graph depicting average lymph vessel size quantification of 10 representative vessels from 3 WT, 3 Rpl27a$^{low/+}$, 2 Mdm2$^{+/-}$, 2 Mdm4$^{+/-}$, 3 RP27M2, and 3 RP27M4 mice. Statistical significance determined by t test. NS (not significant), *p<0.05, p<0.01, and *p<0.001. FIG. 5B Panel d shows dorsal embryonic skin double stained with Ki-67 and Lyve-1. Magnification 40× for WT and Rpl27a$^{low/+}$, 20× for RP27M2 and RP27M4 embryos. FIG. 5B Panel e shows p21 overexpression in lymphatic endothelium. Data are representative of more than four biological samples per genotype. Scale bars are 100 μm for Panels a, b and e and 50 μm for Panel d.

FIG. 8 shows results indicating that genetic deletion of one copy of p53 in RP27M2 and RP27M4 mice reverses the lymphatic anomalies and rescues embryonic lethality. Panel a shows progeny of Rpl27a$^{low/+}$ mice crossed to Mdm2$^{-/-}$: p53$^{-/-}$ or Mdm4$^{-/-}$:p53$^{-/-}$ mice. Mendelian ratio is re-established. Panel b shows representative images of 9 month old mice. Panel c shows representative images of E16.5 RP27M2:p53$^{+/-}$ and RP27M4:p53$^{+/-}$ embryos showing no cutaneous hemorrhaging or edema. Panel c shows representative images of Lyve-1 immunostaining in E16.5 skin out of 15 imaged vessels per genotype. *Chi-square test reveals no statistical difference between observed and expected progeny numbers. 20× magnification, scale 100 μm.

FIGS. 9A and 9B show results indicating that p53 upregulation inhibits lymphangiogenesis. FIG. 9A Panel a shows mutant pups born at Mendelian ratio from mothers treated with PFT-a do not exhibit cutaneous hemorrhaging and severe edema. FIG. 9A Panel b shows representative H&E staining of PFT-a treated postnatal day 0 (P0) skin. FIG. 9B Panel c shows Lyve-1 staining of PFT-a treated P0 skin.

FIG. 10A Panel a: Hematopoietic CD45$^+$-depleted cell suspensions from skin stained with anti-CD31 and anti-PdPn and analyzed by flow cytometry. FIG. 10B Panel b: Lyve-1 expression on LECs of mutants (dotted lines) and WT control (solid lines) of the respective population. For a-d 15 WT, 8 Rp27a$^{low/+}$, 5 Mdm2$^{+/-}$, 5 Mdm4$^{+/-}$, 7 RP27M2, and 9 RP27M4 samples analyzed in 8 independent experiments. FIG. 10B Panel c: A histogram presenting the frequency of Population III stained with Lyve-1 that decreases significantly in mutant skin. FIG. 10B Panel d: A histogram presenting the frequency of Population III stained with Lyve-1 that reverts to normal WT levels when one p53 allele is deleted. Statistical significance was analyzed by t test. NS: not significant, *p<0.05, p<0.01, and *p<0.001.

FIG. 12 Panel a shows p53 IHC staining of lymphatic endothelium (L) or vein (V) in pediatric lymphedema specimen and panel b shows the same for normal human skin. Panel c shows a table depicting 6 out of 8 human lymphatic cases are highly positive for p53.

FIGS. 14A and 14B show results indicating edema and cutaneous hemorrhaging are progressive and more severe in RP27M4. FIG. 14A Panel a shows images depicting edema (red arrows) and hemorrhaging scoring criteria used by three researchers during evaluation to avoid bias. FIG. 14B Panel b shows graphs depicting severity scoring of edema by gestational age. FIG. 14B Panel c shows graphs depicting severity of hemorrhaging by gestational age. Sample sizes for (FIG. 14A Panel a) and (FIG. 14B Panel b) are at E13.5: 10 RP27M2 and 14 RP27M4; at E14.5: 38 WT, 42 Rpl27a$^{low/+}$, 25 Mdm2$^{+/-}$, 36 Mdm4$^{+/-}$, 32 RP27M2, and 38 RP27M4; at E15.5: 31 WT, 33 Rpl27a$^{low/+}$, 14 Mdm2$^{+/-}$, 19 Mdm4$^{+/-}$, 30 RP27M2, and 10 RP27M4 embryos. Statistical significance determined by one-way ANOVA (for the first panels of a & b) and t tests. NS=not significant, *p<0.05, p<0.01, and *p<0.001.

FIG. 17 shows in Panel a severity of lymphatic phenotypes based on sex: WT (M=14, F=9), Rpl27a$^{low/+}$ (M=28, F=25), Mdm2$^{+/-}$, (M=19, F=14), Mdm4$^{+/-}$, (M=11, F=8), RP27M2 (M=10, F=18), and RP27M4 (M=7, F=8). Statistical significance determined by t test. NS (not significant), *p<0.05, p<0.01, and *p<0.001. Panel f shows a schematic of proposed mechanism of action of p53 on lymphatic development. In Panel b is a schematic of proposed mechanism of action of p53 on lymphatic development showing the p53 upregulation inhibits proliferation of lymphatic vessels resulting in insufficiency of lymphatic drainage and cutaneous hemorrhaging.

FIG. 18 presents Table 1.
FIG. 19 presents Table 2.
FIGS. 20A and 20B present Table 3.
FIG. 21 presents Table 4.

DETAILED DESCRIPTION

Lymphedema is an incurable, disfiguring, and often debilitating disease. It develops due to abnormalities in the formation and/or function of the lymphatic system, which results in the accumulation of protein-rich fluid (lymph) in the interstitial space and swelling. Onset can vary from embryonic stages to middle age. Many lymphedema patients struggle with self-esteem, psychological pain, and low quality of life. Left untreated, lymphedema can lead to chronic and disabling infections and inflammation. Examples of disorders of primary lymphedema are Milroy's disease, Klippel-Trenaunay and Cloves Syndromes. Here, Applicants describe a new pathway for development of lymphedema. This pathway is useful in identifying novel targets for treatment of lymphatic disorders, in particular of lymphedemas.

Figure 1:
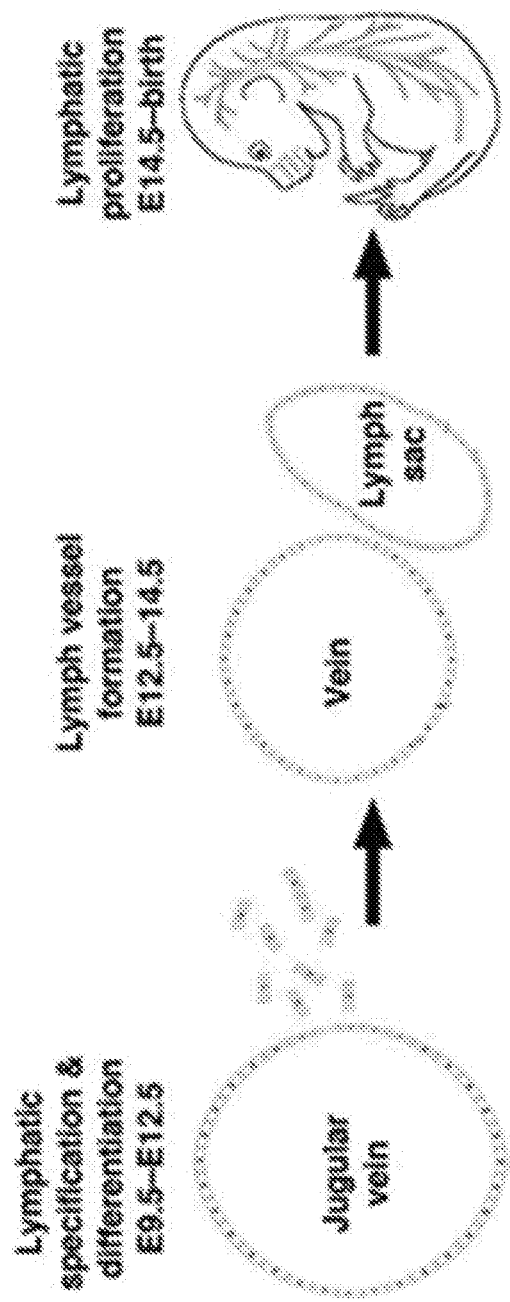
FIG. 1 is an adapted schematic representation of lymphatic development.

The lymphatic system drains lymph from interstitial spaces, absorbs lipids from the intestines, and transports immune cells. Abnormalities in this network can result in inherited and congenital disorders characterized by edema of the skin and extremities. During development, Lymphatic Endothelial Cells (LECs) arise from veins to form primary lymph sacs that then proliferate and sprout to establish independent lymphatic vessels and capillaries (FIG. 1). Blood and lymphatic systems form in close proximity and are kept separate through the lymphovenous junction (LV) to prevent mixing of blood and lymph. LV is where lymph drains into blood. The lymphovenous valve (LVV) prevents the backflow of blood into the lymphatic vasculature. Thus, lymph vessels ultimately cover the entire body and remain largely separated from the blood circulation. Genetic models with lymphatic abnormalities have uncovered a number of key factors involved in lymphatic development. Prospero homeobox 1 (Prox-1), Vascular Endothelial Growth Factor C (Vegf-3/Vegfc), and Podoplanin (Pdpn), among others, are critical regulators of lymphatic network development. Despite recent progress, the field lacks a comprehensive picture and has yet to fully establish the molecular determinants of lymphatic vasculature development, or the factors that keep it separated from blood vessels.

Figure 3:
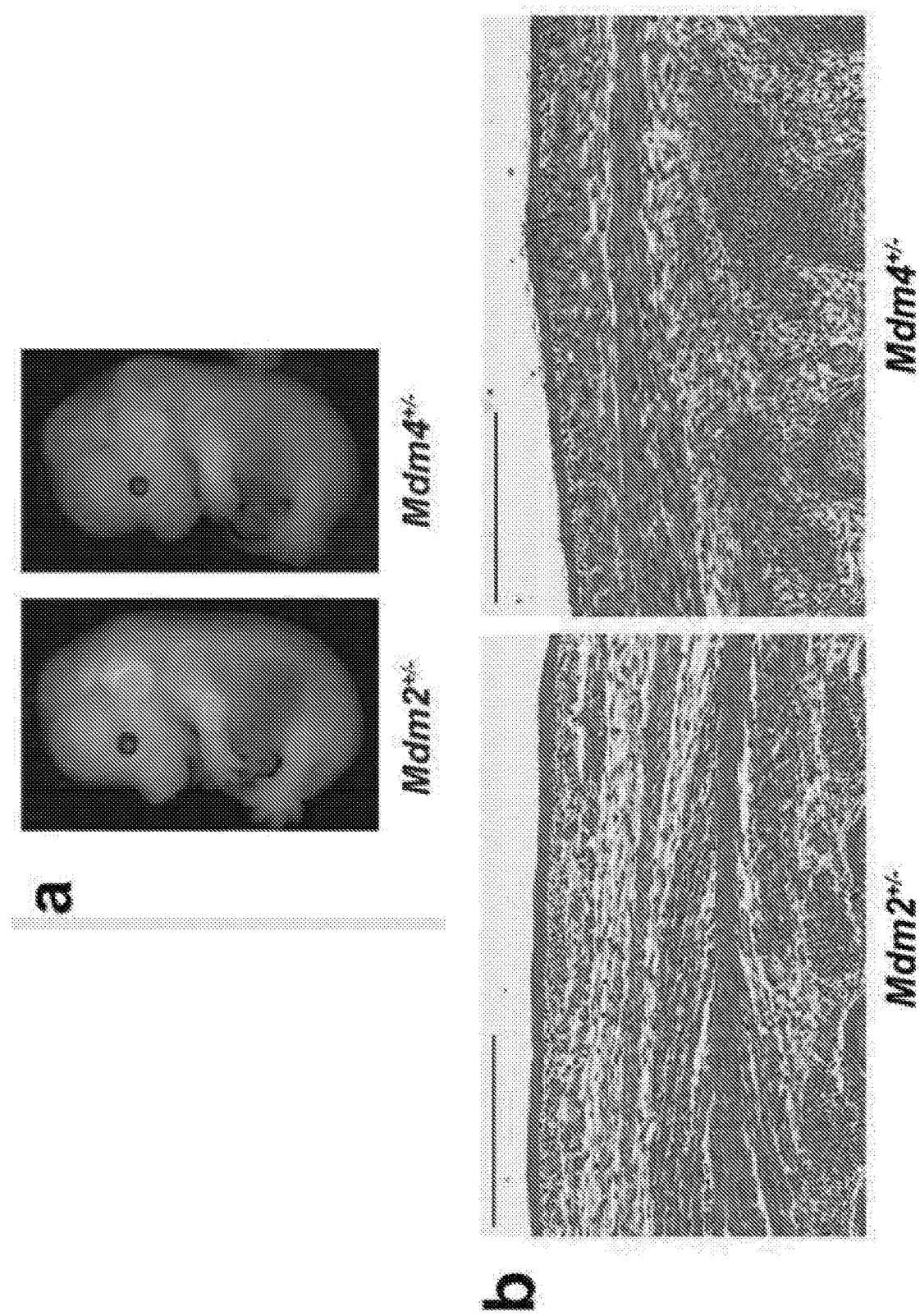
FIG. 3 shows results indicating E14.5 Mdm2$^{+/-}$ and Mdm4$^{+/-}$ embryos are normal. Panel a shows representative images taken with Leica M165 FC stereoscope. Panel b shows H&E staining of dorsal skin. Scale bar represents 300 μm.
Figure 4A:
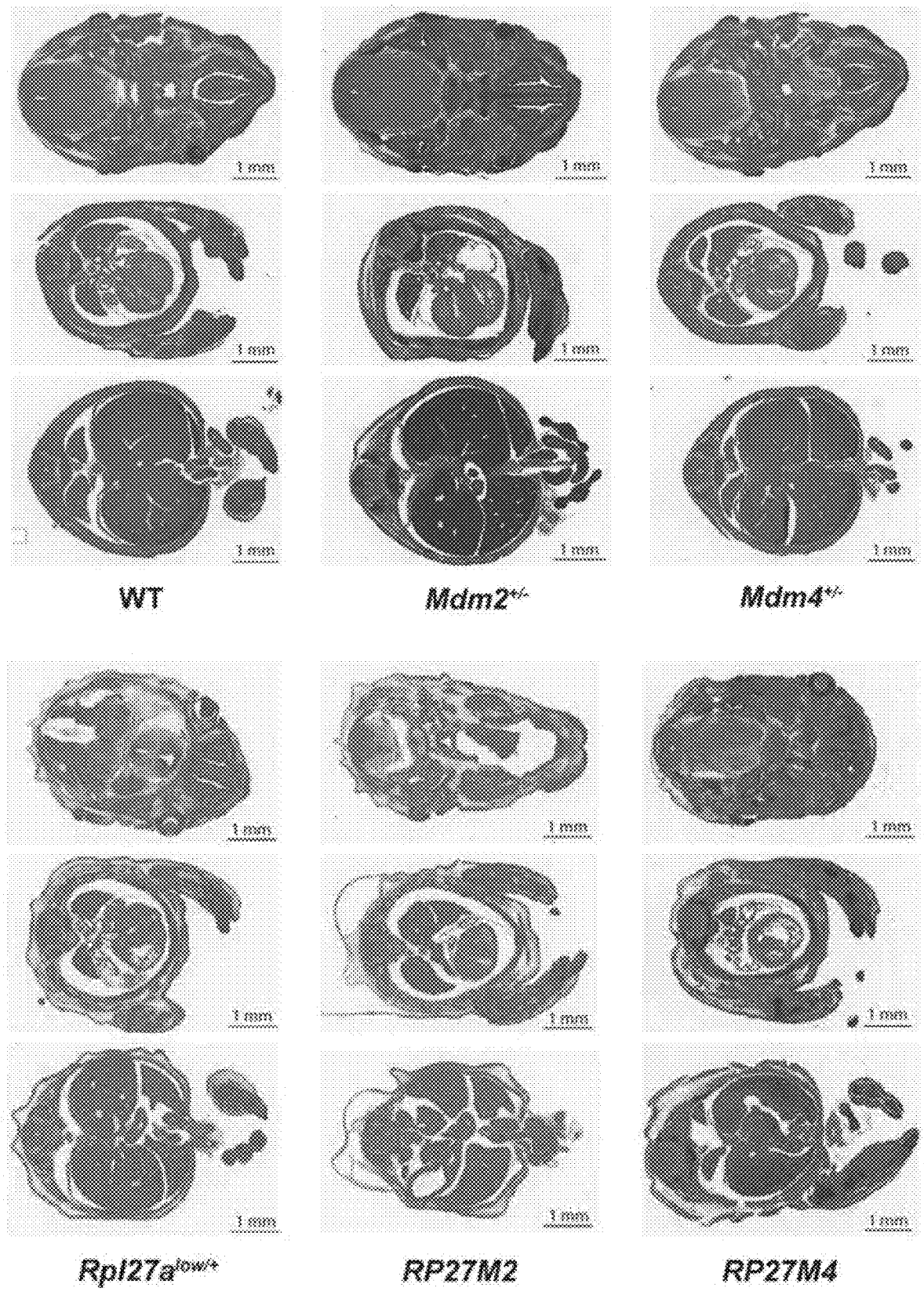
Figure 5A:
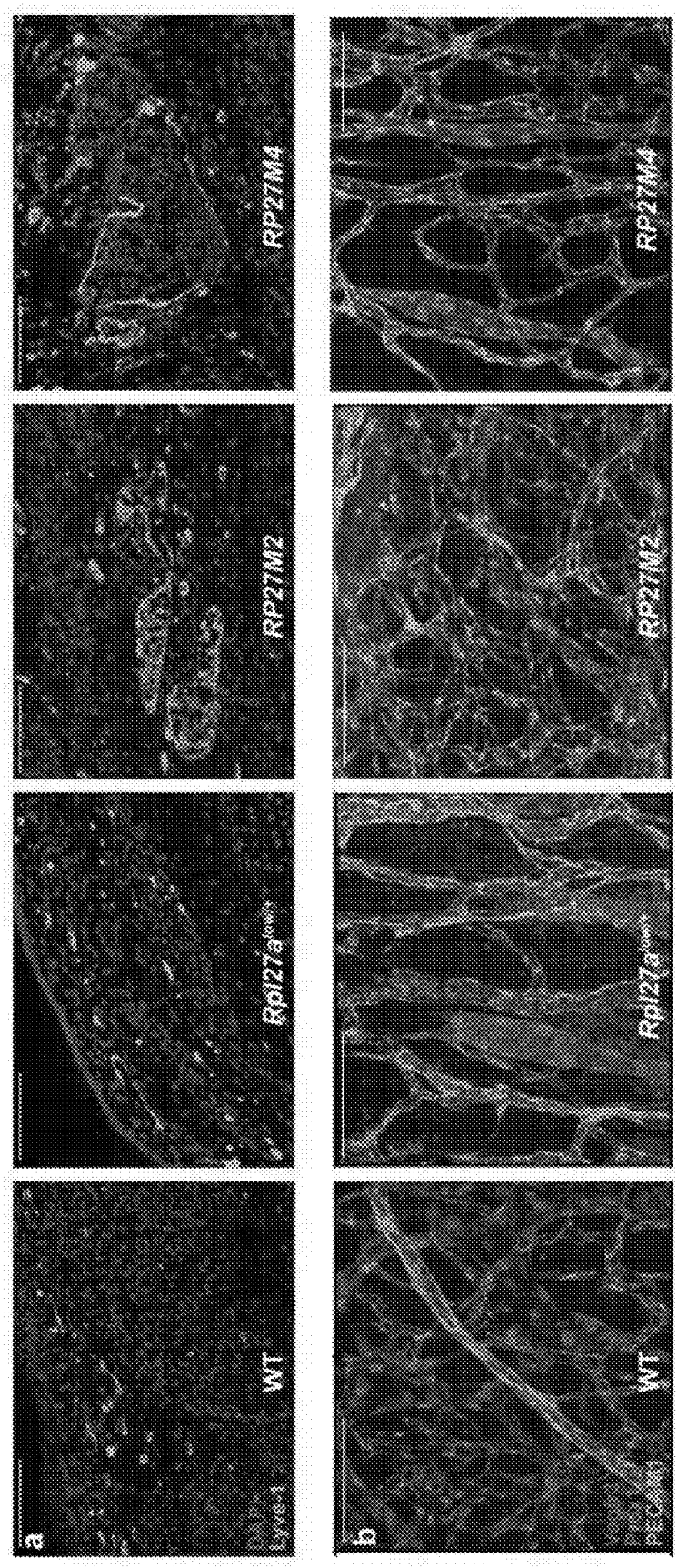
FIGS. 5A and 5B show enlarged E14.5 and E15.5 cutaneous lymphatic endothelium.
Figure 5B:
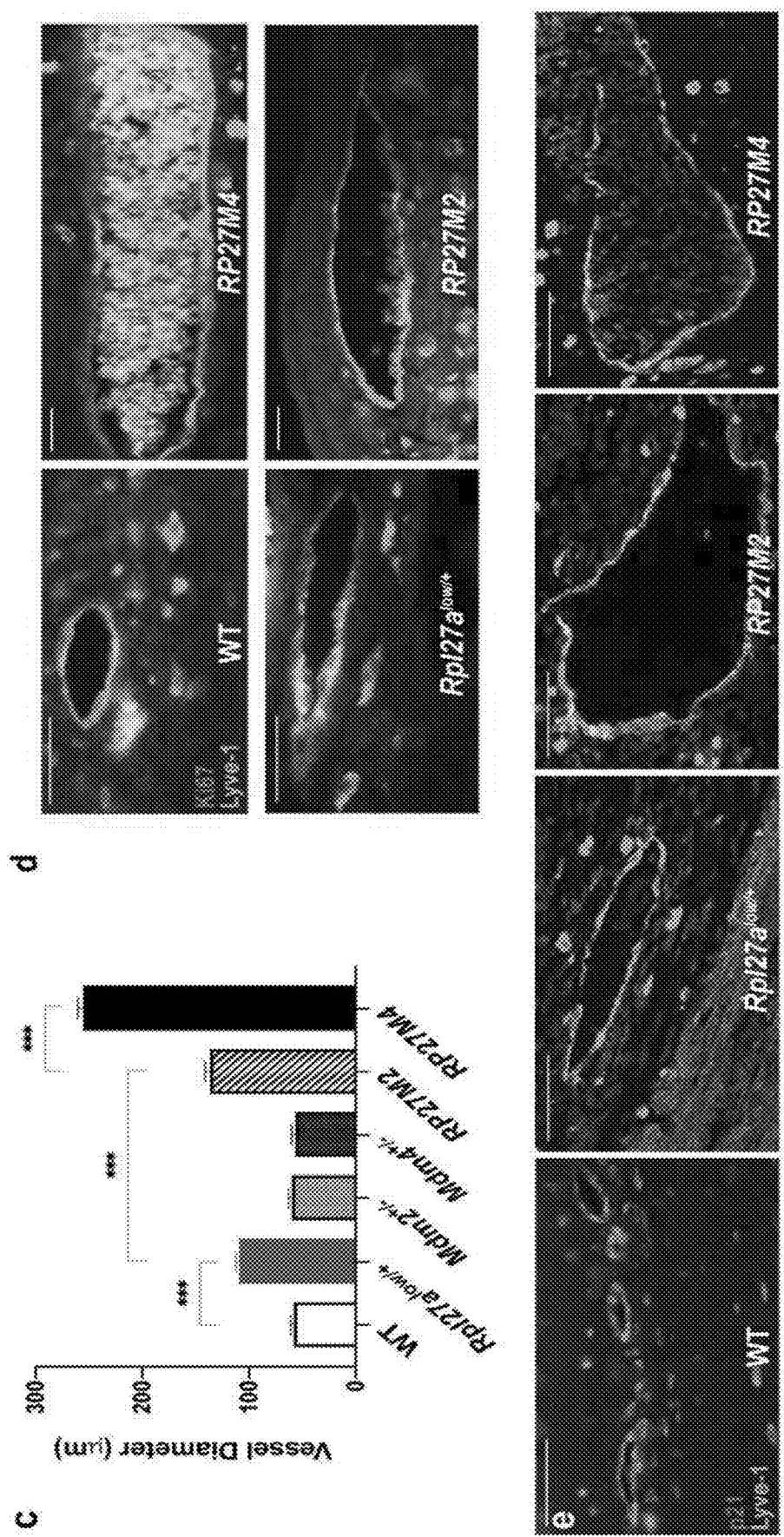
Figure 6:
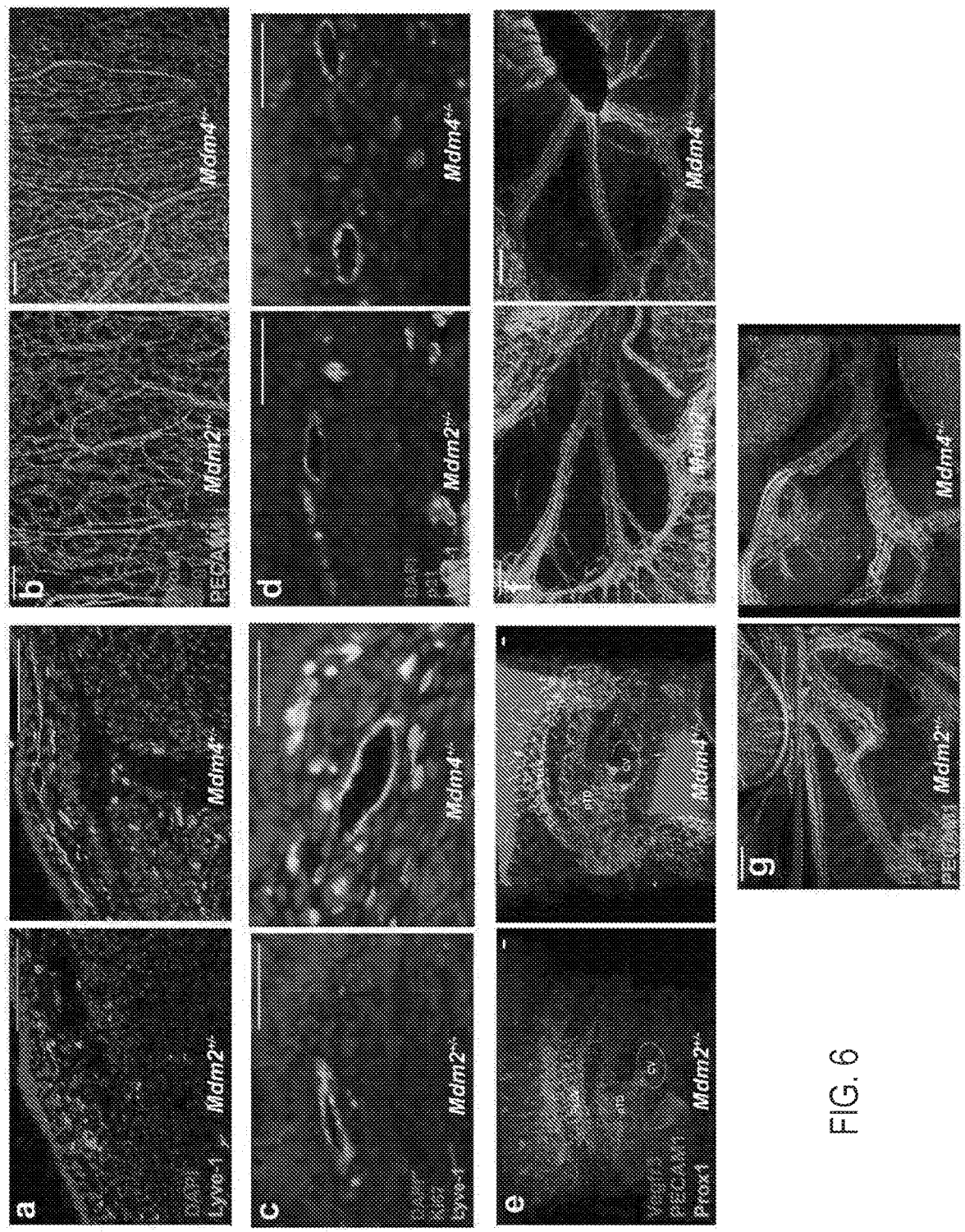
FIG. 6 represents IF staining of Mdm2$^{+/-}$, and Mdm4$^{+/-}$ skin that shows normal size lymphatic vessels comparable to WT. Panel a shows Lyve-1 staining of E15.5 skin. Panel b shows whole-mount staining of E14.5 skin. Panel c shows Ki-67 and Lyve-1 double staining of E15.5 skin. Panel d shows p21 and Lyve-1 double staining of E15.5 skin. Panel e shows Ultramicroscopy imaging of E11.5 CV, pTD and superficial LECs. Panel f shows whole-mount staining of E14.5 mesentery and panel g shows the same of E16.5 mesentery.
Figure 7:
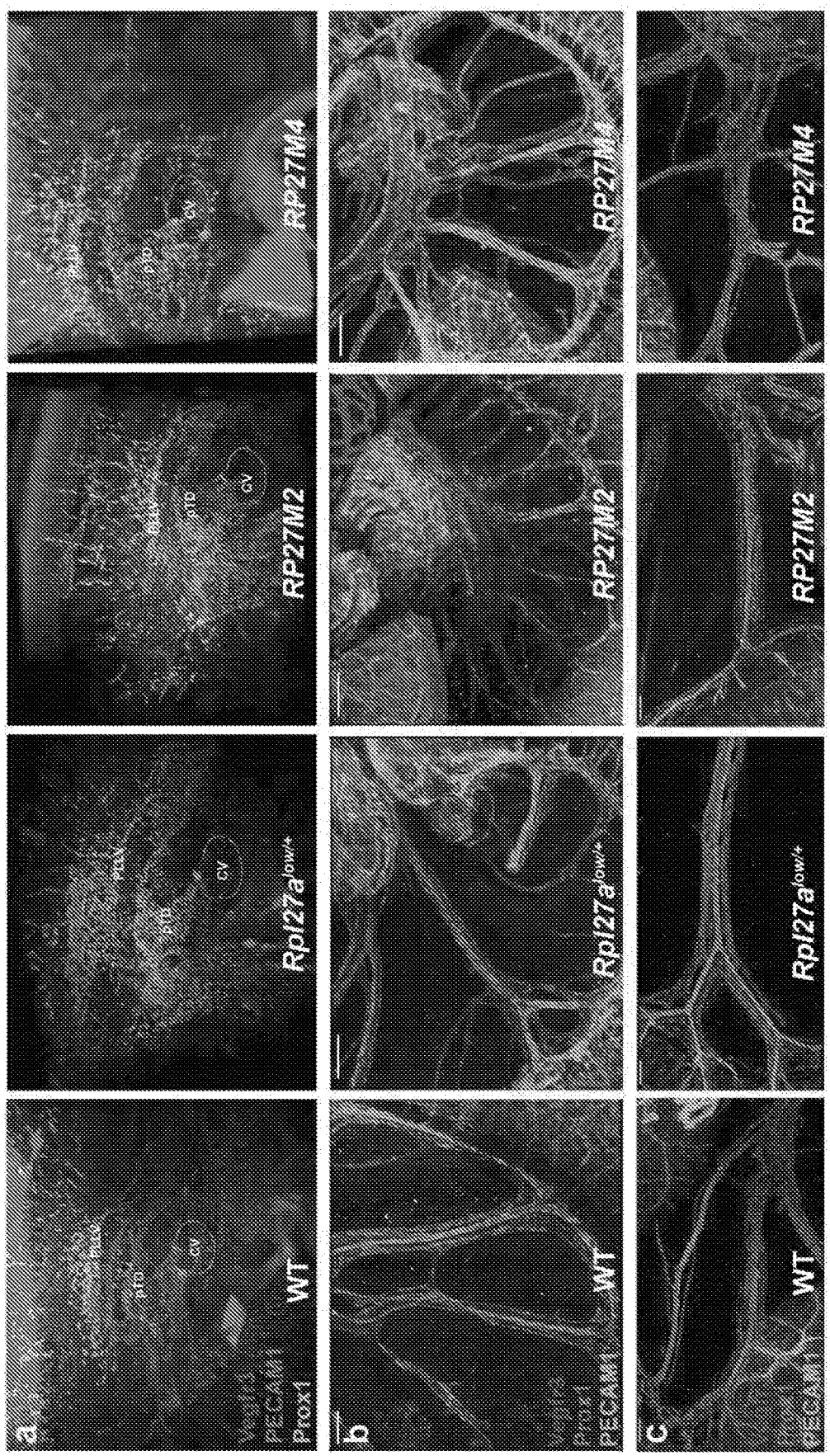
FIG. 7 shows lymphatic vessels in mutant embryos are less dense or absent but show no obvious defects in early embryogenesis a) Ultramicroscopic imaging of the E11.5 embryo visualizes the primordial thoracic duct (pTD), Peripheral Longitudinal Lymphatic Vessels (PLLV), Primordial Valves (PV), Cardinal Vein (CV), and superficial LECs. b) Confocal images of whole-mount E14.5 mesenteries and c) E16.5 mesenteries. Scale bars are 100 μm.

Applicants have examined genetic interactions between Rpl27a and Mdm2 or Mdm4. For example, to study the effects of ribosomal stress induced p53 during embryonic development, compound mice were created with low Rpl27a and heterozygosity for Mdm2 or Mdm4. During these studies it was noted that double heterozygous mice (Mdm2$^{+/-}$: Rpl27a and Mdm4$^{+/-}$:Rpl27a) died between embryonic days 14.5 (E14.5) and E16.5 of gestation (FIG. 2 Panels a-b; Tables 1-2 at FIGS. 18 and 19). Detailed examination of the embryos revealed severe vasculature defects at mid-gestation (equivalent to the third trimester in pregnant women) near complete penetrance (~100%), which was accompanied by cutaneous edema and hemorrhaging (FIG. 2 Panels c-d; FIG. 3 Panels a-b). Surprisingly, Applicant's histopathological assessment did not reveal visible defects in major organs such as the brain, heart or liver (FIGS. 4A and 4B). In addition, trichrome staining for collagen fibers, muscle and bone in whole embryos did not show obvious abnormalities (data not shown). Further examination indicated severely hyper-dilated skin lymphatic vessels that contained a significant amount of blood (FIG. 5A and FIG. 5B Panels c) compared to control littermates (FIG. 6 Panel a) and delay in the development of mesentery lymphatics (FIG. 6 Panels b, f, g and FIG. 7 Panels b-c)

The characteristics seen in these mutants phenocopy mice having defects in lymphangiogenesis where the differentiation of lymph vessels from blood vessels is failing (Fu et al. J, JCI 2008, Deng Y et al. JCI, 2013). Importantly, as the immune system of a fetus does not develop during this stage, the observed phenotypes do not appear to result from immune deficiency.

Figure 9B:
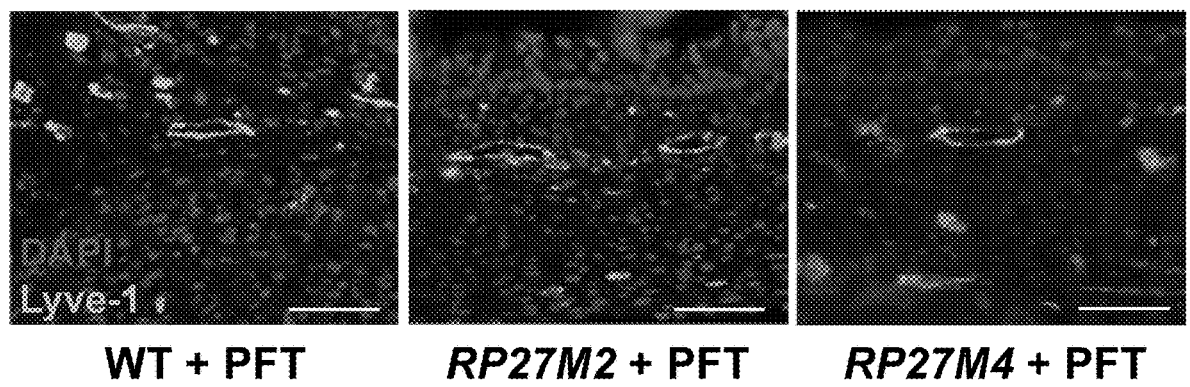

Applicants show that the observed embryonic lethality in these mice may be rescued by either genetic deletion of p53 (Mdm2$^{+/-}$:Rpl27a:p53$^{+/-}$, and Mdm4$^{+/-}$:Rpl27a:p53$^{+/-}$ mice) (FIG. 8) or pharmacological inhibition of p53 (e.g. by administration of Pifithrin-α, or PFT, and cyclic-Pifithrin or c-PFT) (FIGS. 9A and 9B). These findings suggest that the pathologic dilation of lymph vessels (or lymphangiectasia), or defects in lymphatic development more generally, seen in these mice may be due to elevated levels of p53. Moreover, the data also suggest that it may be possible to manage this condition by bringing p53 activity and levels back to normalcy and physiological levels through genetic or pharmacologic treatment.

Applicants disclose that major functional activities of p53 were tested in lymphedemic skin from Mdm2$^{+/-}$:Rpl27a and Mdm4$^{+/-}$:Rpl27a mice, including programmed cell death or apoptosis and cell cycle arrest, and gene expression from major target genes was tested. Appoptosis was not observed, however, lymphedemic tissue showed a block in lymphatic tissue proliferation along with increased expression of the major p53 target gene, p21 (Cdkn1a). This finding indicates that pharmacologic targeting of p21 or other p53 target genes may help with management or treatment of lymphedema.

Disclosed herein is the use of PFT or c-PFT to help reduce venous and/or lymphatic defects in a subject suffering from these conditions. In some embodiments, the disease or condition may be lymphangiectasia. Reducing the activity of p53 may include lowering or interfering with the level of expressed p53 protein, p53 gene transcription, p53-DNA binding affinity, p53-based gene transcription, etc. Reducing activity of p53, in most embodiments, may reduce the activity (transcription, translation, DNA-binding, etc.) to less than about 95%, 90%, 85%, 80%, 75%, 70%, 65%, 60%, 55%, 50%, 45%, 40%, 35%, 30%, 25%, 20%, 15%, 10%, 5%, or 1%, of wild-type p53 or of the activity found in subjects with wild-type p53, and greater than about 0.1%, 1%, 5%, 10%, 15%, 20%, 25%, 30%, 35%, 40%, 45%, 50%, 55%, 60%, 65%, 70%, 75%, 80%, 85%, 90%, or 95%.

Disclosed herein is the use of butyrolactonel (BL), LLW10, sorafenib, UC2288 or other drug that targets p21 to help reduce venous and/or lymphatic defects in a subject suffering from these conditions. In some embodiments, the disease or condition may be lymphangiectasia. Reducing the activity of p21 may include lowering or interfering with the level of expressed p21 protein, p21 gene transcription or translation, p21 protein interaction or binding affinity, p21-based cell cycle regulatory functions, etc. Reducing activity of p21, in most embodiments, may reduce the activity (transcription, translation, DNA-binding, etc.) to less than about 95%, 90%, 85%, 80%, 75%, 70%, 65%, 60%, 55%, 50%, 45%, 40%, 35%, 30%, 25%, 20%, 15%, 10%, 5%, or 1%, of wild-type p21 or of the activity found in subjects with wild-type p21, and greater than about 0.1%, 1%, 5%, 10%, 15%, 20%, 25%, 30%, 35%, 40%, 45%, 50%, 55%, 60%, 65%, 70%, 75%, 80%, 85%, 90%, or 95%.

Disclosed herein is a newly discovered role for p53 activity in lymphangiogenesis that has not been previously recognized. In some embodiments, p53 activity may play a role in mid-to-late gestation. In many embodiments, p53 activity may affect skin vascular remodeling, and that modulation of p53 activity may help prevent, manage, or treat cutaneous lymphatic and venous pathologies in subject in need of same. In some embodiments, cutaneous lymphatic and venous pathologies that may lead to edema. The disclosed compositions and methods may be useful in treating various conditions and disorders, involving the lymph system, for example primary lymphedema. In some embodiments, the disclosed methods and compositions may be useful in preventing, managing, or treating various conditions or diseases including Milroy's disease, Klippel-Trenaunay and Cloves Syndromes.

Various compounds with inhibitory effect on the function of p53 may be used in the disclosed methods, protocols, and processes. In some embodiments the compound is a pharmaceutical compound. In various embodiments, the compound is a pifithrin, for example pifithrin-α (PFT or PFT-α; 2-[2-Imino-4,5,6,7-tetrahydrobenzothiazol-3-yl]-1-p-tolylethanone hydrobromide], or pifithrin-β (cyclic pifithrin-α), pifithrin-µ (PFT-µ), ReACp53, PK11000, and pharmaceutically acceptable forms thereof, such as cyclic pifithrin-α hydrobromide.

Pifithrin-α (PFT or PFT-α; 2-[2-Imino-4,5,6,7-tetrahydrobenzothiazol-3-yl]-1-p-tolylethanone hydrobromide] is a compound that is soluble in the apolar solvent DMSO (dimethyl sulfoxide; $[CH_3]_2SO$). PFT has been shown to block activity of p53. Below is shown the structure of PFT:

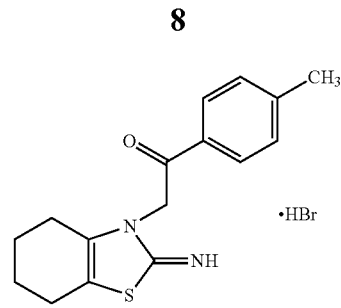

Cyclic pifithrin-α hydrobromide, molecular weight 349.29, is a bromide salt of cyclic pifithrin-α, and a transcriptional inhibitor of p53. Cyclic pifithrin-α results from condensation of Pifithrin-alpha. In most embodiments, cyclic pifithrin-α is more stable and less cytotoxic than other pifithrin. In some cases, cyclic pifithrin-α is named cyclic-pifithrin or pifithrin-beta (PFT-β). Cyclic pifithrin-α has been shown not to promote tumor development (Leonova K I et al. 2010, Cell Cycle). In other embodiments, alternative acceptable forms of cyclic pifithrin-α may be used in the disclosed methods. The structure of cyclic pifithrin-α hydrobromide is:

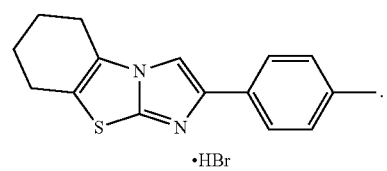 [SMILES: Cc1ccc(-c2cn3c4c(sc3n2)CCCC4)cc1 ; Br]

A pharmaceutically acceptable carrier may comprise water, glycerin, petrolatum, stearic acid, glycol stearate, dimethicone, isopropyl isostearate, tapioca starch, cetyl alcohol, glyceryl stearate, magnesium aluminum silicate, carbomer, ethylene brassylate, triethanolamine, disodium EDTA, phenoxyethanol, methyl paraben, propyl paraben, ethanol, bio-polymers (e.g., sodium hyaloronate), liposomes, nano- and micro-particulate carriers, and/or titanium dioxide. In some embodiments, the pharmaceutically acceptable carrier comprises dimethyl sulfoxide (DMSO), glycerol, propylene glycol, and petrolatum water.

As used herein, "phenocopy" may refer to an organism sharing one or more phenotypes, traits, and/or characteristics with a different organisms, wherein the shared phenotypes may or may not be due to the same or similar genetic factor(s).

As used herein, "wild-type" or "wt" may refer to a gene or protein that is at least about 95% homologous to a form of the gene or protein found in nature. In some cases, wild-type may refer to an organism homozygous for a given wild-type gene, for example a human.

Example 1—p53 Overexpression

We generated two mouse models that overexpress p53 triggered by ribosomal stress and loss of p53's main inhibitors: Mdm2 (RP27M2) or Mdm4 (RP27M4). During development, p53 is kept low since it has anti-proliferative activity.

Figure 2:
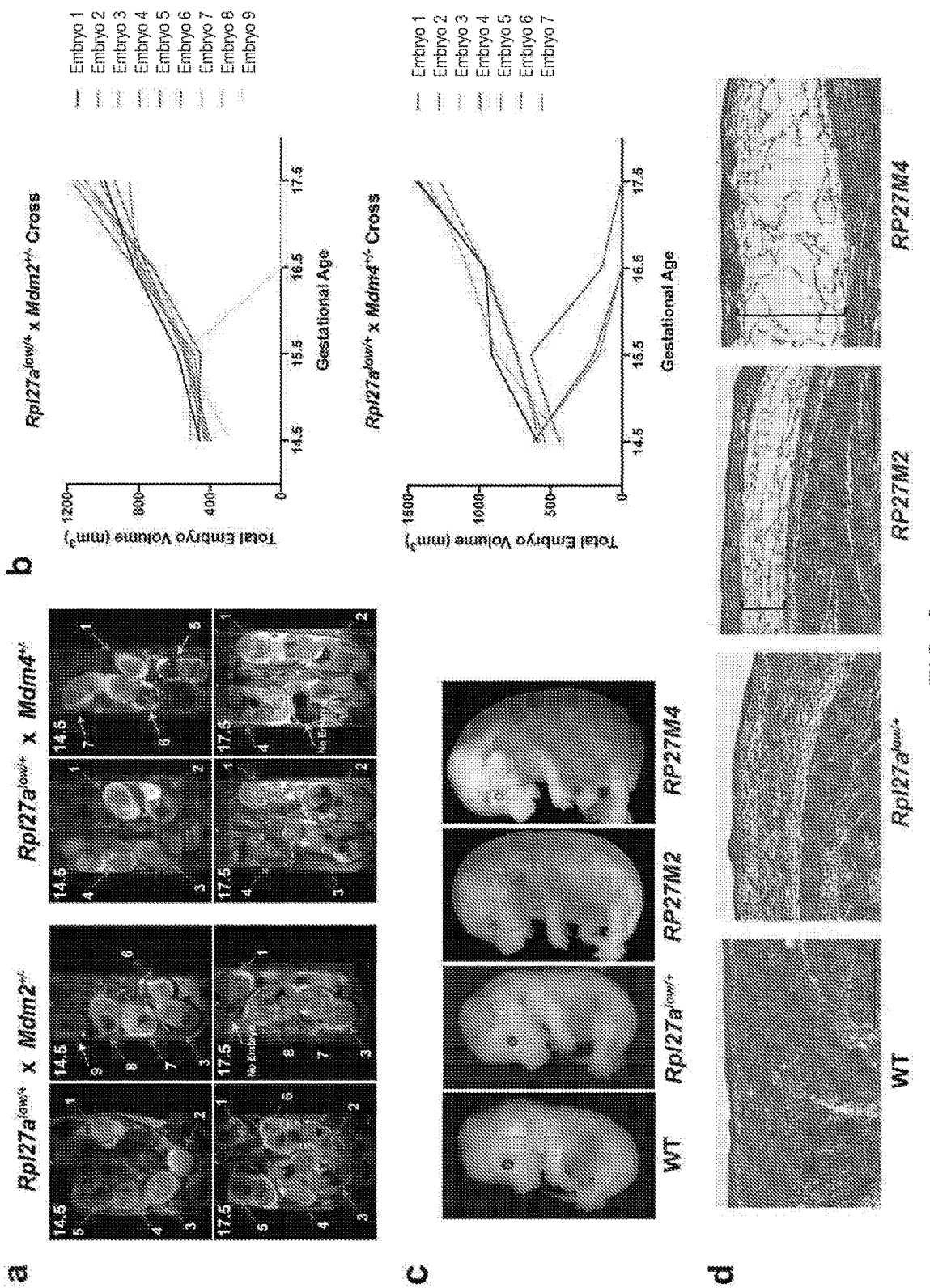
FIG. 2 shows results from double heterozygous RP27M2 or RP27M4 mice that are embryonic lethal due to severe edema and cutaneous hemorrhaging. Panel a shows MRI scans of Mdm2$^{+/-}$ and Mdm4$^{+/-}$ pregnant mice showing coronal sections of fetuses fathered by Rpl27a$^{low/+}$ males. Red arrows point to embryos that survived and yellow ones to embryos terminated before E17.5. Panel b shows plots of embryonic volumes as pregnancy progresses. Panel c shows embryonic images at E15.5. Panel d shows H&E staining of E14.5 back skin. Scale bars are 300 μm. Black brackets show subcutaneous edema.
Figure 20A:
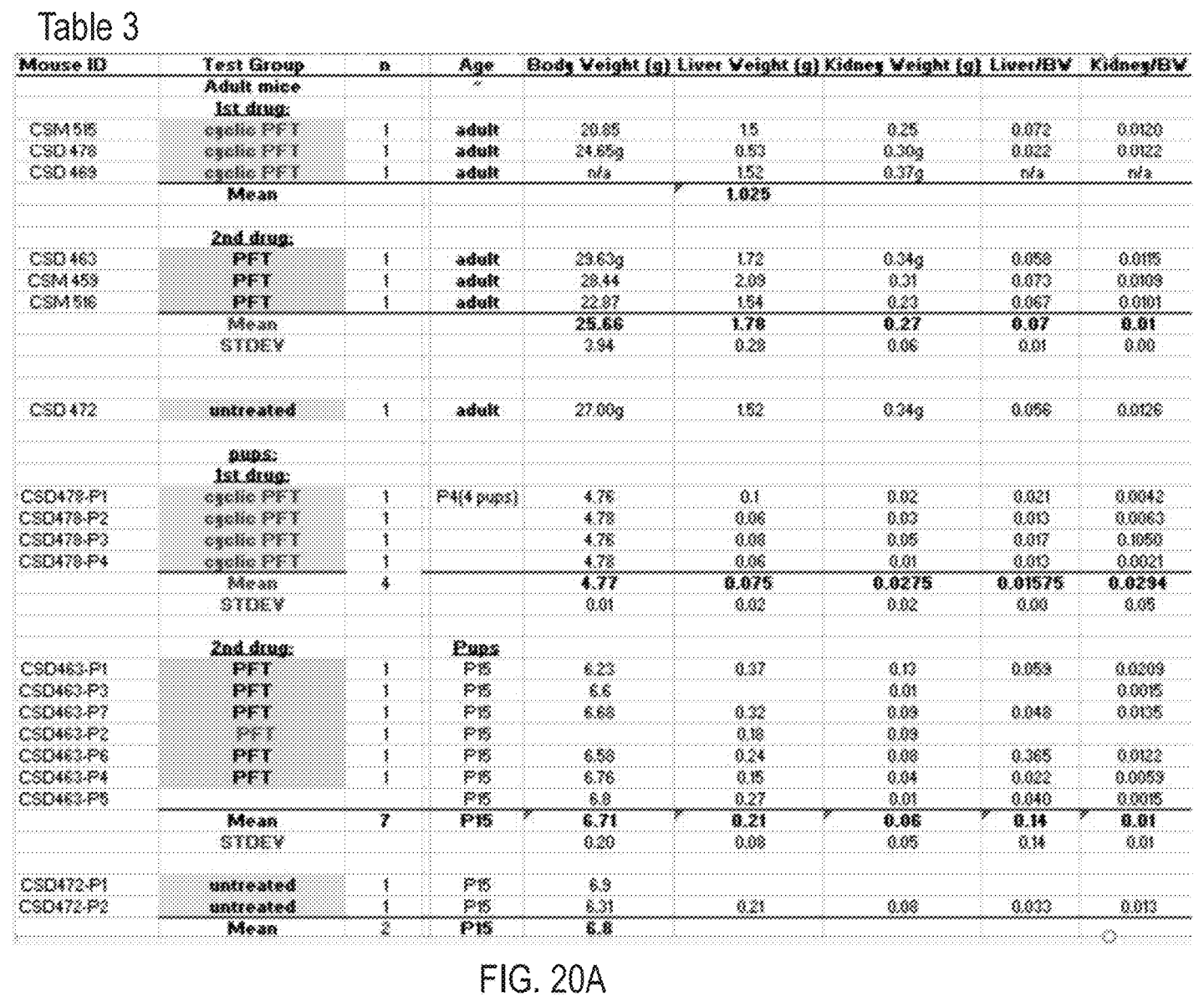
Figure 20B:
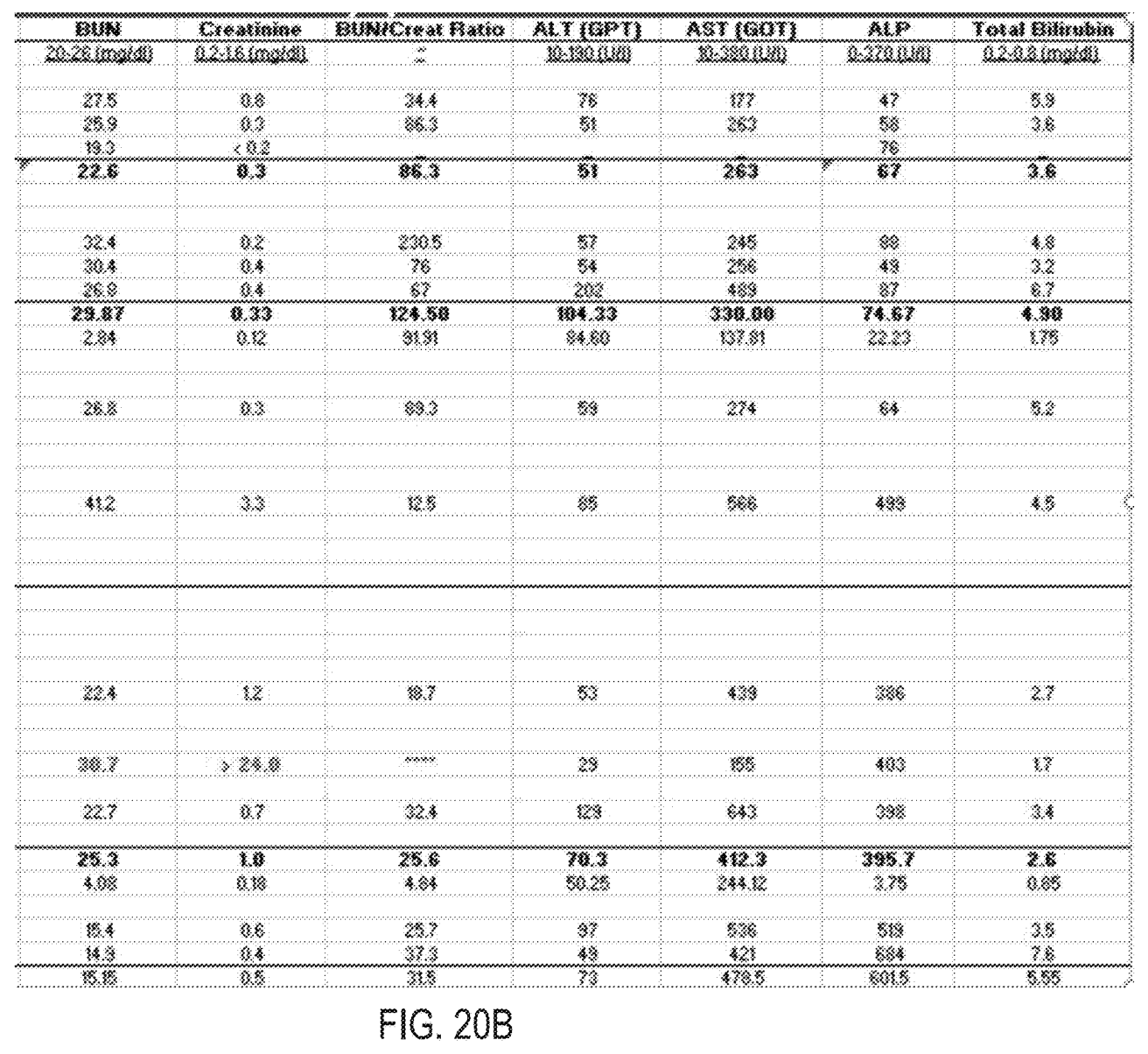

The two models exhibit severe edema and hemorrhaging at very high penetrance (>90%) at the developmental timepoints E14.5 to E16.5 (FIG. 2 Panel c). These embryos do not survive beyond E16.5. Immunostaining of RP27M2 skin shows distended lymphatic vessels filled with blood and accumulation of fluid and hemorrhage under the epidermis (FIGS 5A, 5B and FIG. 6 Panels a, c, d). Interestingly, these phenotypes appear to be restricted to the skin per pathological examination, with no apparent defects in major organs (e.g. heart, liver and lung). These data highlight the important role that the cutaneous lymphatic vasculature plays in the genesis of lymphedema and the necessity for furthering research in this field. More importantly, the two models of p53 identify the p53 tumor suppressor as a new molecular regulator of lymphatic vascular formation in the skin. In fact, genetic deletion of one copy of p53 suppresses all phenotypes, allowing ostensibly normal development until adulthood (FIG. 8). Moreover, daily pharmacologic inhibition of p53 via systemic delivery of the specific inhibitor of p53, PFT (FIGS. 9A and 9B) or c-PFT (Tables 3-4 at FIGS. 20A, 20B and 21), to pregnant mice of both models eliminates visible skin hemorrhaging and rescues in utero lethality (treatment from E11.5-delivery, FIGS. 9A and 9B).

Applicants, herein, describe a new and potentially central role for p53 in skin lymphatic vascular formation during embryonic development. In some embodiments, inhibition of p53 activity (for example by genetic or pharmaceutical treatment, e.g. PFT, c-PFT, PFT-μ and ReAcp53) may be effective in the prevention, management, or treatment of lymphatic conditions such as lymphedema. Applicant's present findings are consistent with the known role of p53 as a stress sensor and master transcriptional guardian of cellular and genomic integrity.

The disclosed embryonic models of lymphedema revealed p53-driven lymphatic vascular abnormalities as well as methods and compositions for treating lymphedema.

Figure 10A:
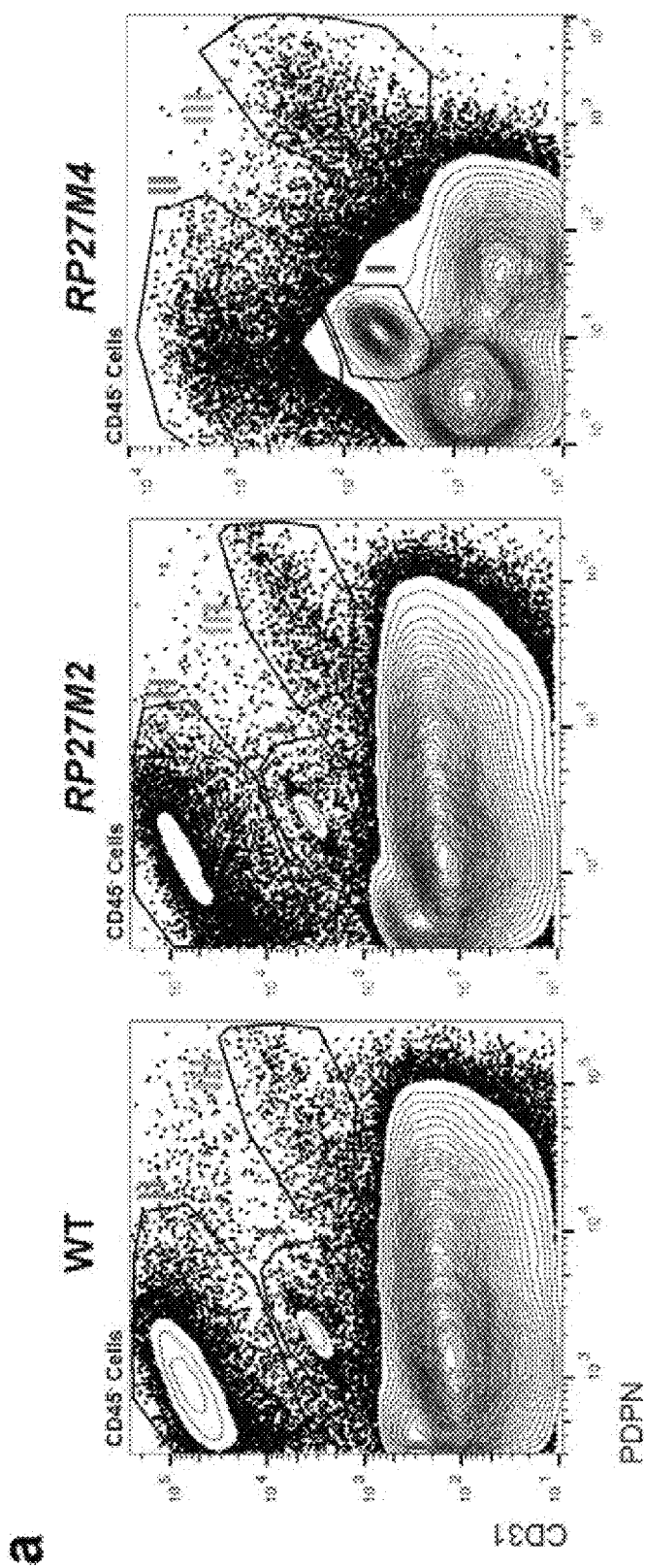
FIGS. 10A and 10B depict Flow cytometry analysis of RP27M2 and RP27M4 skin showing the presence of distinct endothelial cell populations.

Example 2—Differential Gene Expression of Endothelial Cells from Normal and Edemic Skins Putative BECs and LECs from E12.5-E15.5 skin samples (without pooling) were sorted by flow cytometry. Briefly, embryonic skin was harvested under a stereoscope and placed in EHAA media without L-glutamine (Gibco). Skin was cut into 1 mm sized pieces, and digested for 45 minutes at 37° C. by 0.25 mg of Liberase DL (Roche) per ml of EHAA media and DNAse (Worthington). An equal volume of 0.1 M EDTA in Hank's buffered saline solution without Calcium or Magnesium was added to the digested cells and incubated for 5 min at 37° C. Digested skin was passed through a 100 μm strainer and washed with 5 mM EDTA, 2.5% FBS in EHAA. Stromal cells were stained with CD45 (clone 30-F11), PDPN (clone 8.1.1), CD31 (clone 390) and Lyve-1 (clone 223322). Stromal cell subsets are identified based on their lack of CD45 expression and the expression of PdPn and CD31. As blood endothelial populations do not express Pdpn, we classified the blood endothelium as (CD45− Pdpn− CD31$^{mid}$ or hi) and lymphatic endothelium as (CD45− Pdpn+ CD31+). We then looked at Lyve-1 expression on these cell types in WT and mutant mice. Cells were run on the DakoCytomation CyAn ADP flow cytometer (Fort Collins, Colo.), acquired using Summit acquisition software and analyzed with FlowJo software (Tree Star, Ashland, Oreg.). Lymphatic vasculature normally expresses CD31+ Pdpn+ and Lyve-1 (Population III), while blood vasculature does not express Pdpn or Lyve-1 (Populations I & II) (FIG. 10 Panel a). This concept is based on the observation that in the mutant mice, CD45− CD31$^{mid}$ Lyve-1+ Pdpn− cells (Population I) uniquely accumulate, while Populations II begins expressing Lyve-1. Population III (the putative LECs) express similar levels of Lyve-1 and their numbers decrease slightly (FIG. 10 Panels b-c).

Data show no cellular differences between WT and mutant skin prior to E14.5, while at E15.5 Population I expands and Population II disappears (FIG. 10 a). However, we do not know the exact identity of these cells and identifying the transcriptome of Populations I-III and defining how they are altered is of utmost importance. Of a note, tissue resident Macrophages are often very Lyve1+ and would express low levels of CD31, however, they are excluded by CD45 in the sort.

Example 3—Over-Expression of p53 in Pediatric Lymphatic Malformation Tissue Samples The endothelium arteries and veins detected with the endothelial marker CD31 (Dako), stain negatively for p53 in lymphatic malformations (FIG. 11), while lymphatic endothelium cell nuclei stained very positively. Experimental result above suggests p53 is acting as a stress sensor during development, where its aberrant activation disrupts the normal progression of lymphatic vessel formation.

Figure 11:
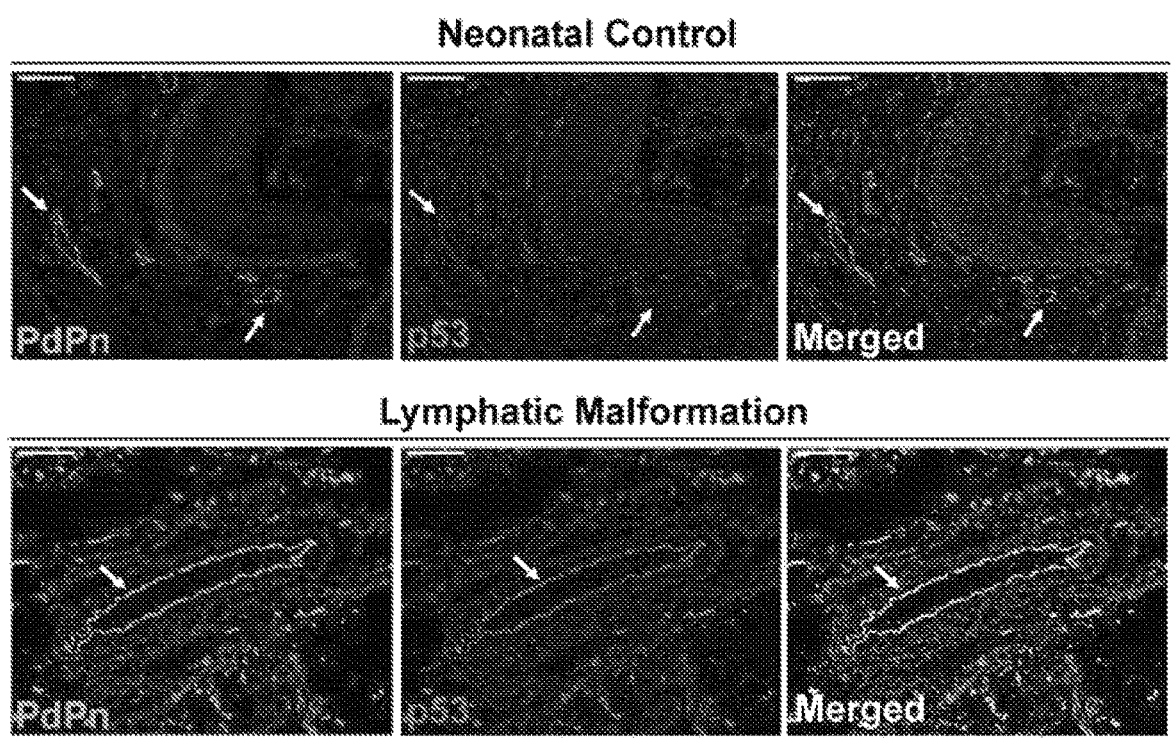
FIG. 11 shows PdPn and p53 immunostaining of lymphedema-associated Lymphatic Malformation and neonatal skin control. Figure shows that lymphatic endothelium is positive for p53 in human lymphatic disease and negative in normal adult endothelial tissue.

These studies identified p53 overexpression in 6 out of 8 lymphatic disease tissue (FIGS. 11 and 12).

Example 4—Materials and Methods

Figure 13:
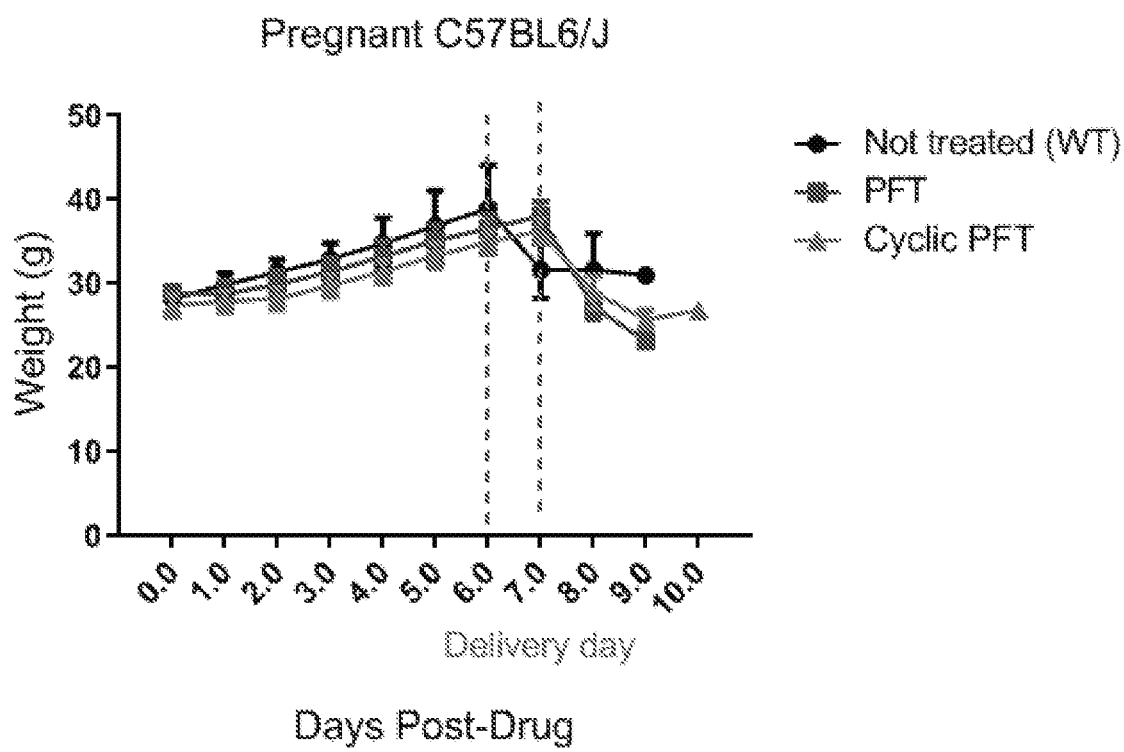
FIG. 13 is a graph depicting weight of mice during study.

All mice were maintained on a C57BL/6J background. For timed pregnancies, the first day of observed plug were recorded as day 0.5 post-coitum or embryonic day 0.5 (E0.5). Mice haploinsufficient for the ribosomal protein L27a (Rpl27$^{low/+}$) are crossed with Mdm2 or Mdm4 heterozygous mice (Mdm2$^{+/-}$ or Mdm4$^{+/-}$) to generate WT, Rpl27$^{low/+}$, Mdm2$^{+/-}$, Rpl27$^{low/+}$:Mdm2$^{+/-}$ (RP27M2), Mdm4$^{+/-}$, and Rpl27$^{low/+}$:Mdm4$^{+/-}$ mice (RP27M4). To generate mice on a p53-deficient background, we crossed Rpl27$^{low/+}$ mice to Mdm2$^{-/-}$:p53$^{-/-}$ or Mdm4$^{-/-}$:p53$^{-/-}$ mice. We therefore obtained RP27M2:p53$^{+/-}$ mice and RP27M4:p53$^{+/-}$ mice (FIG. 8). Genotypes were determined by PCR analysis of extracted DNA from tails using published primer sets for Mdm2, Mdm4, and p53. The sex of embryos was determined by detection of Sry and Raspn genes by PCR. Animal care and euthanasia guidelines of the Colorado Institutional Animal Care and Use Committee were followed for all animal work. FIG. 13 shows weight post administration and green dashed lines show delivery dates.

A 10 mM stock of Pifithrin-α (PFT-α, Selleck Bio, cat. S2929) was diluted 1:10 in 1×PBS, protected from light and used instantly. Pregnant mice were injected intraperitoneally from E11.5 to E16.5 and subcutaneously from E17.5 until delivery at 2.2 mg/kg of weight. Animal were monitored daily post-treatment and weights were recorded after delivery.

Tissues were fixed in 4% neutral buffered paraformaldehyde, processed, and embedded in paraffin by the UCD Research Histology core. Sagittal sections (5 μm) were subjected to immunofluorescence staining (IF) as previously described and according to the manufacturer's recommendations. The primary antibodies used for IF were monoclonal mouse Prox-1 (1:50, P21936, Thermofisher Scientific, Massachusetts, USA), monoclonal rabbit Lyve-1 (1:100, ab14917, Abcam Inc., California, USA), polyclonal rabbit Ki-67 (1:1000, VP-K451, Vector Laboratories, California, USA) and mouse monoclonal p21 (1:100, sc-6246, Santa Cruz Biotechnology, California, USA) antibodies. We used anti-rabbit or anti-mouse Alexa Fluor 594 or Alexa Fluor 488 conjugated secondary antibodies (1:1000, Invitrogen, California, USA), captured the images on a Nikon Eclipse 90i, and quantified using the ImageJ software. Pediatric lymphatic edema was categorized using the ISSVA Classification of Vascular Anomalies and confirmed by PdPn (D2-40 antibody, Ventana or RnD Systems AF3670) staining. IHC for p53 on human tissues were performed using the D-07 antibody (Ventana) on automated strainers (Ventana Ultra) following the manufacturer's recommendations and Clinical Laboratory Improvement Amendments (CLIA) certified procedures. For the visualization of the three-dimensional lymphatic vasculature, murine skin were fixed in 4% Paraformaldehyde (PFA) for 2-4 hours at room temperature for whole mount staining. Tissues were then subjected to procedures as published. H&E was performed following Harris protocols for staining.

Mouse embryonic skins were placed in RNA Later (Sigma, cat. R0901) overnight at 4° C., then stored at −80° C. until RNA was extracted. 5 mg of skin was homogenized in 20% 0.4M DTT in RLT Lysis Buffer (Qiagen, Hilden, Germany). The RNA was isolated using the RNeasy Plus Micro Kit (cat. 73404 and 74004, Qiagen, Hilden, Germany) and their corresponding protocol. Samples with an RNA concentration greater than 500 ng/µL and A280/260 ratio 1.8-2.0 were used for cDNA synthesis. cDNA of 100 ng/µL concentration was synthesized using the SuperScript III First Strand Synthesis SuperMix Kit (cat. 18080-051, ThermoFisher Scientific, Massachusetts, USA). qPCR was performed with Apex Probe Master Mix (cat. 42-116P, Genesee, California, USA), TaqMan Gene Expression Probes (Thermofisher Scientific, Massachusetts, USA), and mouse Gapdh (ref. 4352339E, ThermoFisher Scientific, Massachusetts, USA) used as reference. The reactions were run on a BioRad CFX96 Real Time C1000 Touch ThermoCycler and the gene expression fold change was determined via the ΔCT method. The probes we used were designed for the following target genes: Lyve-1 (Mm00475056_m1), Prox-1 (Mm00435969_m1), c-Kit (Mm00445212_m1), Trp53 (Mm01731290_g1), Mdm2 (Mm01233136_m1), Bbc3 (Puma, Mm00519268_m1), and Pmaip1 (Noxa, Mm00451763_m1).

Embryonic skins of E12.5-E15.5 dpc were harvested using a stereoscope and placed in EHAA media without L-glutamine (Irvine Scientific). Skin was cut into 1 mm sized pieces and digested for 45 minutes at 37° C. by 0.25 mg of Liberase DL (Roche) per mL of EHAA media and DNAse (Worthington). An equal volume of 0.1 M EDTA in Hank's buffered saline solution without calcium or magnesium was added to the digested cells and incubated for 5 min at 37° C. Digested skin was passed through a 100 µm strainer and washed with 5 mM EDTA, 2.5% FBS in EHAA. Stromal cells were stained with CD45 (clone 30-F11), PdPn (clone 8.1.1), CD31 (clone 390), and Lyve-1 (clone 223322). Stromal cell subsets were identified by the expression of PdPn and CD31 and the lack of CD45 expression. Blood endothelium populations were classified as $CD31^{mid\ or\ high}$ PdPn$^-$ CD45$^-$. In contrast, lymphatic endothelium cells were categorized as CD31$^+$ PdPn$^+$ CD45$^-$. Cells were run on the DakoCytomation CyAn ADp flow cytometer (Fort Collins, Colo.) or BD FACS Canto II, acquired using Summit acquisition software and analyzed with FlowJo software (Tree Star, Ashland, Oreg.).

Statistical differences were analyzed using t tests, Chi-Square or one-way ANOVA on Graph Pad Prism 8 software. A P value of 0.05 or lower was considered significant.

Example 5—Genetic Interaction Between Rpl27a, Mdm2, and Mdm4

Mice haploinsufficient for Mdm2, Mdm4, or Rpl27a displayed an endogenously stable p53 resulting in p53-dependent cellular outcomes such as apoptosis and cell cycle arrest. These conditions were subsequently rescued by the deletion of one copy of p53. To test for potential genetic interactions between these genes and observe the impact of an augmented p53 activity, Rpl27a$^{low/+}$ mice were crossed to Mdm2$^{+/-}$ or Mdm4$^{+/-}$ animals. From hundreds of crosses, the expected double heterozygotes were not observed (Rpl27a$^{low/+}$:Mdm2$^{+/-}$ (RP27M2) or Rpl27a$^{low/+}$:Mdm4$^{+/-}$ (RP27M4)). Timed mating (E11.5-E18.5) indicated the presence of these genotypes until E16.5 (Tables 1-2 at FIGS. 18 and 19).

MRI imaging (FIG. 2 Panel a) confirmed these observations and detected the termination of mutant embryos as indicated by the gradual decrease of volume to 0 mm$^3$ between E15.5-E17.5 (FIG. 2 Panel b). As genotyping could not be done in utero, the deceased embryos during MRI were presumed to be the double heterozygotes not seen at birth. All the other genotypes developed normally with an increase in total volume proportional to the gestational age. These findings demonstrate the existence of a genetic interaction between the three genes that ultimately results in fetal lethality.

Figure 14B:
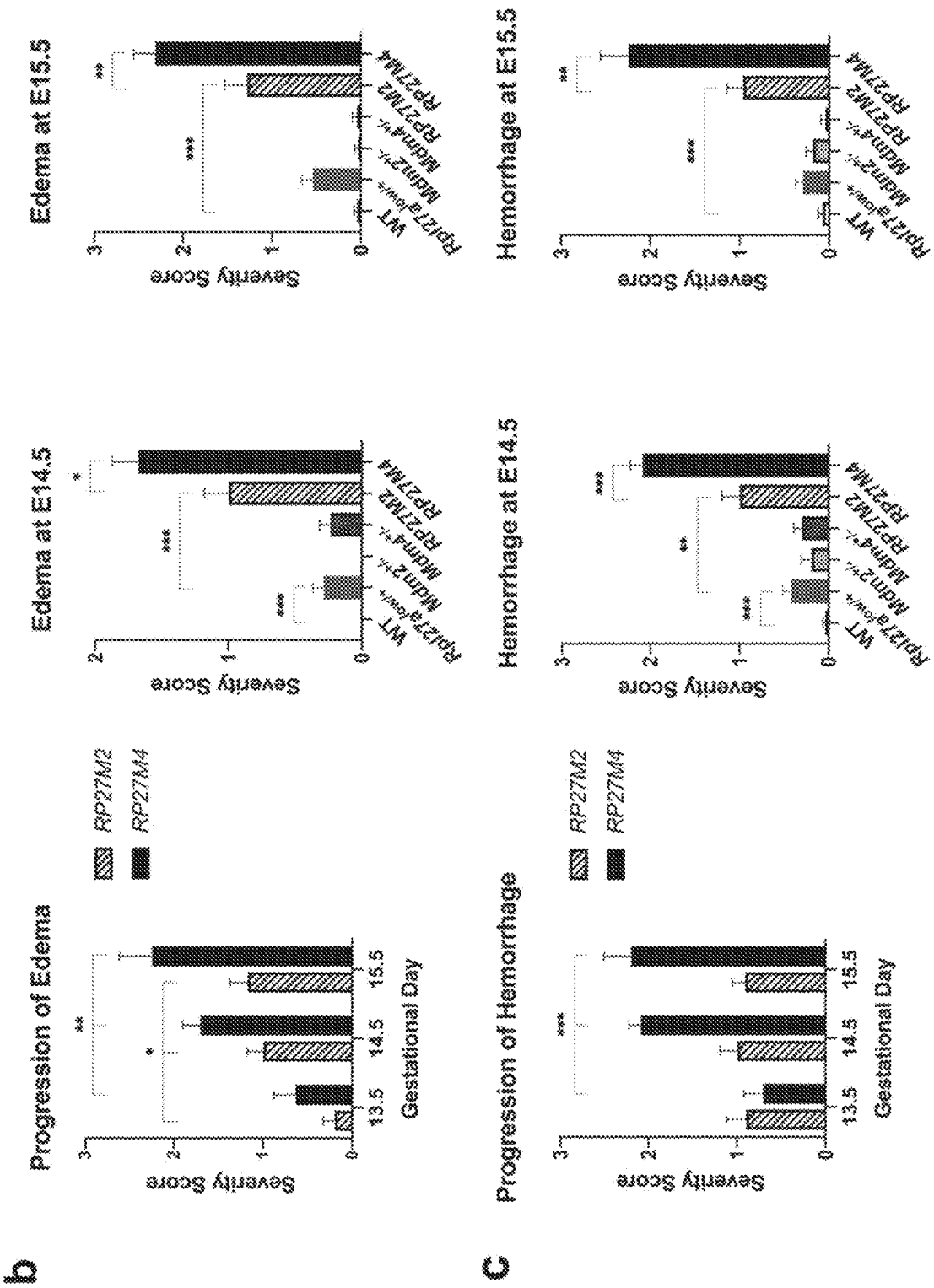

A closer examination showed that Mdm2$^{+/-}$ and Mdm4$^{+/-}$ embryos were similar to WT with no overt phenotypic abnormalities (FIG. 2 Panels c-d; FIG. 3). Rpl27a$^{low/+}$ embryos displayed occasional light hemorrhaging and edema starting at E14.5 that was predominantly localized to the dorsal skin (FIG. 2 Panels c-d, FIG. 4A Panel a). These embryos were born at a lower body weight and with a developmental delay that persisted until around 8 weeks of age. They were able to recover from the delay, reproduce and live normally though maintaining a slightly lower body weight. On the other hand, 100% of RP27M2 and RP27M4 embryos exhibited hemorrhage and/or edema at late-gestation that resulted in 100% mortality post-E16.5 (FIG. 2 and Tables 1-2 at FIGS. 18 and 19). Typically, other mouse models of edema demonstrate an involvement of the lung, the heart or the liver. Histopathological examination of Hematoxylin and Eosin (H&E) stained sections of major organs such as the heart, lungs, brain or liver of mutant embryos showed no overt abnormalities (FIGS. 4A and 4B). When the bloody skin of both mutants was pulled away, no observe internal hemorrhaging was observed (FIG. 4B). Without meaning to be limited by theory, this reasonably suggests that these phenotypes were restricted to the skin. Looking at the H&E of dorsal skin, large fluid-filled gaps in both models and vessels engorged with blood were observed (FIG. 2 Panel d). Hemorrhaging and edema severity scoring on a scale of 0 (none) to 3 (severe) revealed that these conditions gradually worsened with gestational age and ended by death at E16.5 (FIGS. 14A and 14B). RP27M4 phenotypes were significantly more pronounced than those of RP27M2 (FIG. 14 Panels b-c). This is surprising given that Mdm2 is a more powerful inhibitor than Mdm4 due to its E3 ligase activity that degrades p53. Therefore, typically mice with conditional loss of Mdm2 in several tissues are invariably much sicker and at an earlier time than those with Mdm4 loss.

Example 6—RP27M2 and RP27M4 Mice Display Lymphatic Defects

RP27M2 and RP27M4 mutants displayed severe hemorrhaging and cutaneous edema. Immunofluorescence staining (IF) of blood and lymphatic vessels was performed on embryos using markers such as Platelet Endothelial Cell Adhesion Molecule-1 (PECAM-1 or CD31) and Lyve-1, respectively. Small and flat cutaneous lymph vessels (Lyve-1+) were observed in WT mice, while RP27M2 and RP27M4 lymphatics looked extremely distended and filled with blood (FIG. 5 Panel a). Confocal microscopy on whole-mount embryos stained with lymphatic markers Vegfr-3 and Prox-1 (FIG. 5 Panel b) showed free erythrocytes in the interstitial space of the skin and blood-filled (olive color) lymphatics (Vegfr-3+ and Prox-1+ double stained) in the mutants. Sharply reduced density and networking of lymphatics was also noted when compared to the other genotypes. Changes in the distribution of mutant blood vessels (PECAM-1+) indicated that they may also be affected. However, the apparent reduction of blood vessel density may be secondary and a consequence of the pronounced edema. The mutants seem to have increased number of filopodia extended by the LECs and the BECs compared to WT, giving the impression that blood and lymphatic vessels are aligned (data not shown). This occurrence was not quantified, such that the complete involvement of blood vasculature in the observed phenotypes cannot be excluded. The measures of lymphatic vessel size showed a proportional increase in the severity of the phenotypes. As such, the average vessel diameter for RP27M4 measured ~257 μm, which is approximately two times larger than that of RP27M2 (~138 μm), and ~4.3 times bigger than WT lymphatic vessels (~58 μm). To a much lesser extent, Rpl27a$^{low/+}$ lymphatic vessels were also enlarged (~110 μm) compared to WT vessels and often filled with erythrocytes (FIG. 5 Panel c). Given the anti-proliferative role of p53, E15.5 skin was double-stained for Lyve-1 and the proliferation marker Ki-67 and cell cycle arrest marker p21. WT, Mdm2$^{+/-}$, Mdm4$^{+/-}$ and Rpl27a$^{low/+}$ embryos demonstrated an active proliferation in lymphatic vessels and an absence of cell cycle arrest (FIG. 5 Panels d-e, FIG. 6 Panels c-d). In contrast, RP27M2 and RP27M4 cutaneous lymphatic vessels showed no detectable Ki-67 and significant upregulation of p21 in mutant LECs (FIG. 5 Panels d-e). These results indicate a hindrance in proliferation and growth arrest of lymphatic vessels of both models, which may explain the rudimentary network of lymphatics in the mutants. Four E13.5-E16.5 tissues per genotype were also double stained for Caspase-3 and Prox-1 to check for apoptosis, another major cellular process that may be induced by elevated p53. Both RP27M2 and RP27M4 embryos showed no obvious upregulation of apoptosis in lymphatic endothelium compared to the other genotypes (data not shown). While cell death cannot be ruled out, p53 appeared to be acting on the lymphatic network largely through cell cycle arrest.

Ultramicroscopic imaging of the CV and its connecting structures at E11.5 showed that the primordial thoracic duct (pTD) and the CV were physiologically normal in all embryos. However, the primordial valves, which form the contact side between the pTD and the CV, did not develop properly in RP27M2 and RP27M4 mice (FIG. 6 Panel e and FIG. 7 Panel a). Since several primary lymphedema models showed lymphatic defects in the mesenteries, E14.5 mesenteric vessels of RP27M2 and RP27M4 were checked. Only a few Prox-1+ cells were present at the hilus, but not around the major blood vessels as seen in WT embryos. Very few LECs and reduced lymphatic branching were also noted. The small population of LECs present in Rpl27a$^{low/+}$ and mutant mesenteries were rather concentrated near the lymphatic sac, the structure that gives rise to the lymphatic vessels. Prox-1 staining (red) was also detected outside of blood and lymphatic vessels. These Prox-1+ cells were not of lymphatic or blood fate given the absence of Vegfr-3 or PECAM-1 staining respectively (FIG. 7 Panel b). Without meaning to be limited by theory, it was speculated that these cells may be macrophages that have engulfed Prox-1+ cells; however their exact origin is unknown. Staining of E16.5 mesenteries showed that lymphatic vessels were present in Rpl27a$^{low}$ and RP27M2 mice running in parallel along artery-vein pairs that extend from the mesenteric root. In RP27M4, some lymphatic vessels were observed but looked truncated. These observations indicate that lymphatics eventually develop past E14.5 but with a clear delay to WT and single heterozygous mice (6 Panel g, FIG. 7 Panel c).

Figure 15:
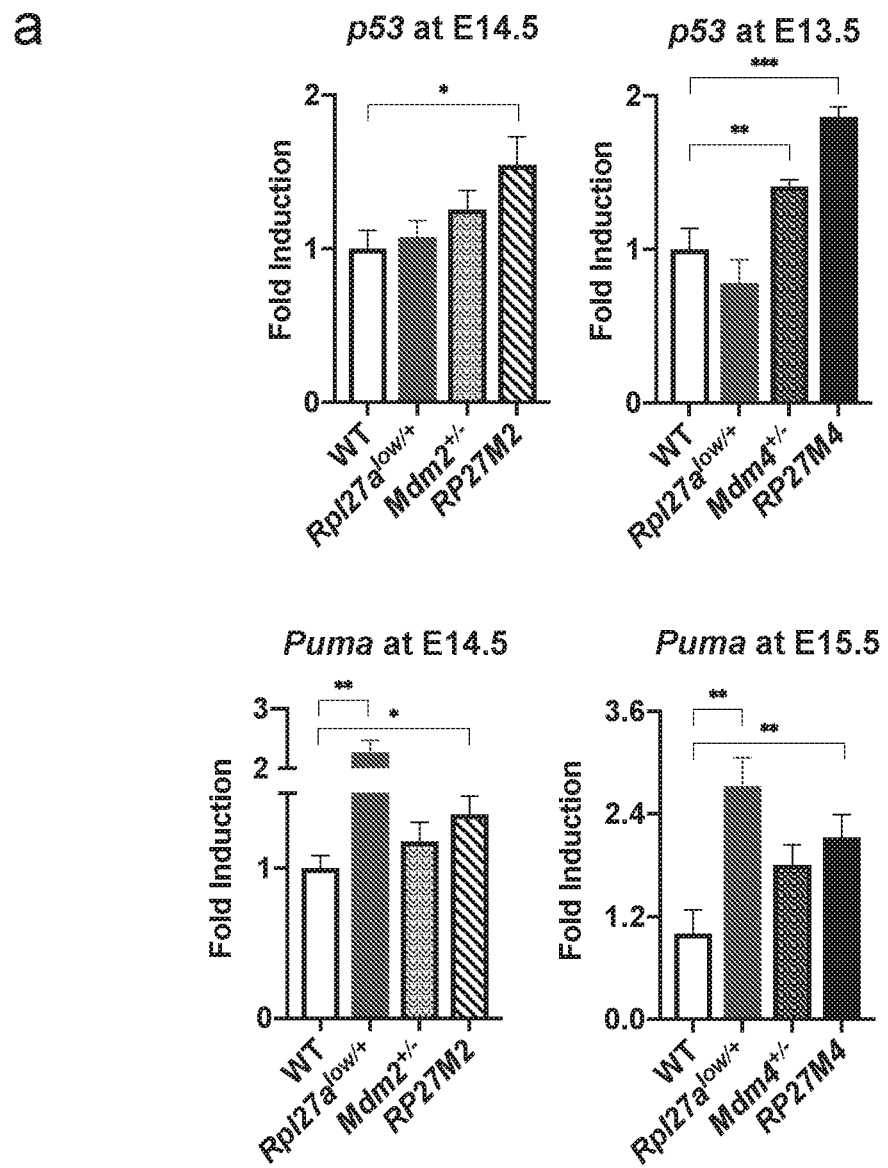
FIG. 15 shows results from gene expression assays by qPCR (mean+SEM) in RP27M2 and RP27M4 skin demonstrates differential expression of p53 targets. N=8 for all genotypes at E13.5, N=6 for all genotypes at E14.5 and N=6-7 at E15.5. Statistical significance determined by t test. NS (not significant), *p<0.05, p<0.01, and *p<0.001.

Gene expression in skin cells of select p53 targets and lymphatic regulators at gestational ages E13.5-E15.5 showed the expected p53 increase in RP27M2 (FIG. 15 Panel a) and a slight but significant upregulation in Puma (p53 upregulated modulator of apoptosis) at E14.5 (FIG. 15 Panel a) that evidently did not translate to increased Caspase-3 positivity in E13.5-16.5 affected tissues (data not shown). Interestingly, p53 overexpression in RP27M4 mice was detected at E13.5 (FIG. 15 Panel a), which was a day earlier than in RP27M2 mice. The surge of p53 at an earlier stage of development in RP27M4 embryos could partially explain the more severe phenotypic presentations. Puma mRNA was also significantly elevated in RP27M4 at E15.5 (FIG. 15 Panel a). Both RP27M2 and RP27M4 skin had dramatically diminished Prox-1 at E15.5 (57% and 73% respectively) in comparison to Rpl27a$^{low/+}$ or WT littermates (FIG. 15 Panel b). Another lymphatic marker Lyve-1 remained elevated at E14.5 and E15.5. Vegfr-3, a Prox-1 target whose expression correlates with lymphatic branching, was reduced in both models at E15.5 (FIG. 15 Panel b). This is consistent with the IF of skin lymphatics that showed fewer lymphatic vessels in mutant mice (FIG. 5 Panel a). Stanczuk et al. (2015) showed that c-Kit+ hemogenic endothelial cells in the mesentery gave rise to lymphatic vessels, indicating that some lymphatics can originate from non-venous hematopoietic progenitors. Since c-Kit is a p53 target that was affected in the mesentery of lymphedema models presented by the Mäkinen group, we checked its levels in the mutants. Amazingly, c-Kit was 80-90% lower in mutant skin compared to WT (FIG. 15 Panel c), suggesting that c-Kit+ hematopoietic progenitors may also contribute as a non-venous source to skin lymphatics. Thus, the reduction in c-Kit can contribute to some extent to the lymphatic abnormalities in both models. However, the accentuated hemorrhaging and edema in RP27M4 mice compared to RP27M2 mice was surprising since Mdm2 is a more powerful inhibitor of p53 than Mdm4. Since Mdm2 also interacts with Mdm4 to regulate p53, the levels of Mdm2 expression in the skin were also analyzed. Strikingly, Mdm2 was very low in RP27M4, which may have resulted in disruption of the Mdm2-Mdm4 interaction and augmented p53 activity induced by Mdm2 and Mdm4 haploinsufficiency (FIG. 15 Panel c). Rpl27a$^{low/+}$ and Mdm4$^{+/-}$ mice also had slightly reduced Mdm2 expression which may have been further exacerbated by the interaction of both genetic conditions as seen in RP27M4 embryos. This could well explain the severity of RP27M4 phenotypes compared to RP27M2. In summary, the findings demonstrated that p53 upregulation from ribosomal stress resulted in low Prox-1, Vegfr-3, and c-Kit, and led to impaired lymphatic development.

To further characterize the endothelial cell populations in E12.5-E15.5 skin of edemic mice, CD45-stromal cells were separated by FACS sorting using the established endothelial markers PdPn, CD31, and Lyve-138-42 (FIG. 10 and data not shown). Four distinct populations were identified: CD31$^{mid}$:PdPn$^{low}$:Lyve-1$^-$ (Population I), CD31$^{high}$:

PdPn$^{low}$:Lyve-1$^-$ (BECs, Population II), CD31$^{mid}$:PdPn$^{high}$:Lyve-1$^{low}$ (LECs, Population IIIA) and CD31$^{mid}$:PdPn$^{high}$:Lyve-1$^{high}$ (LECs, Population IIIB). Prior to E14.5, no significant differences across these populations were detected in WT, RP27M2, and RP27M4 (data not shown). Intriguingly at E15.5, Population I cells drastically accumulated, Population II cells were diminished, and Population III cells were unchanged. A closer look at the state of E15.5 LECs in Population III revealed Lyve-1 low (Population IIIA) and Lyve-1high (Population IIIB) subpopulations. Population IIIB was reduced proportionally to the increase in Population IIIA (FIG. 10 Panel b).

If Population IIIB are the initial lymphatics that absorb the interstitial fluid, their decrease would corroborate the IF skin stains, where lymphatics were reduced in number (FIG. 12 Panel b) and elucidate the edema in RP27M2 and RP27M4 skin. Thus, it is highly likely that the increase in collector lymphatics (Population IIIA), would not sufficiently compensate for the hampering of the formation of initials by merely ramping up the capacity to transport excess fluid back to the vein.

Example 7—Gene Deletion of One p53 Copy in RP27M2 and RP27M4 Mice

Figure 10B:
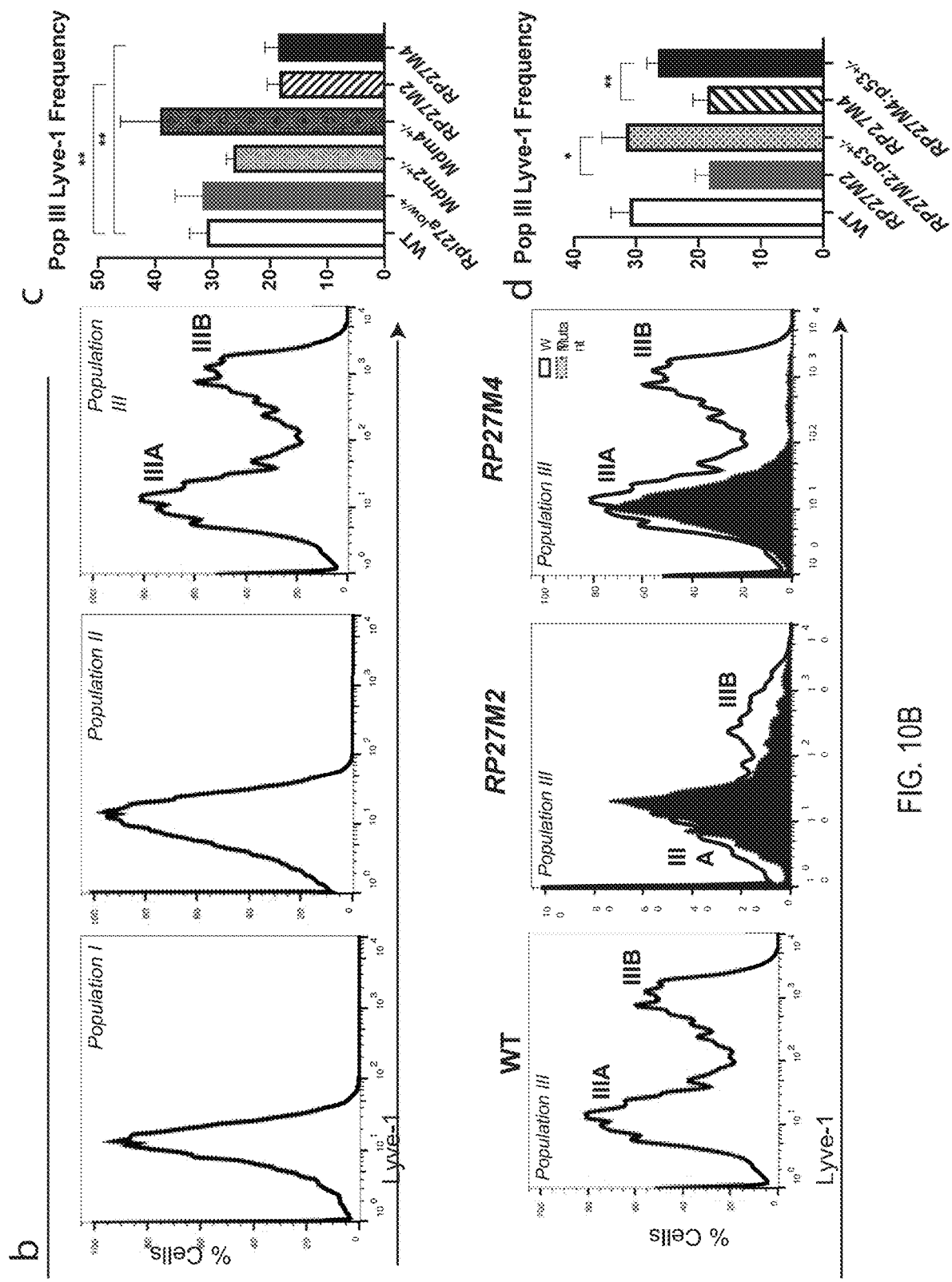
Figure 16A:
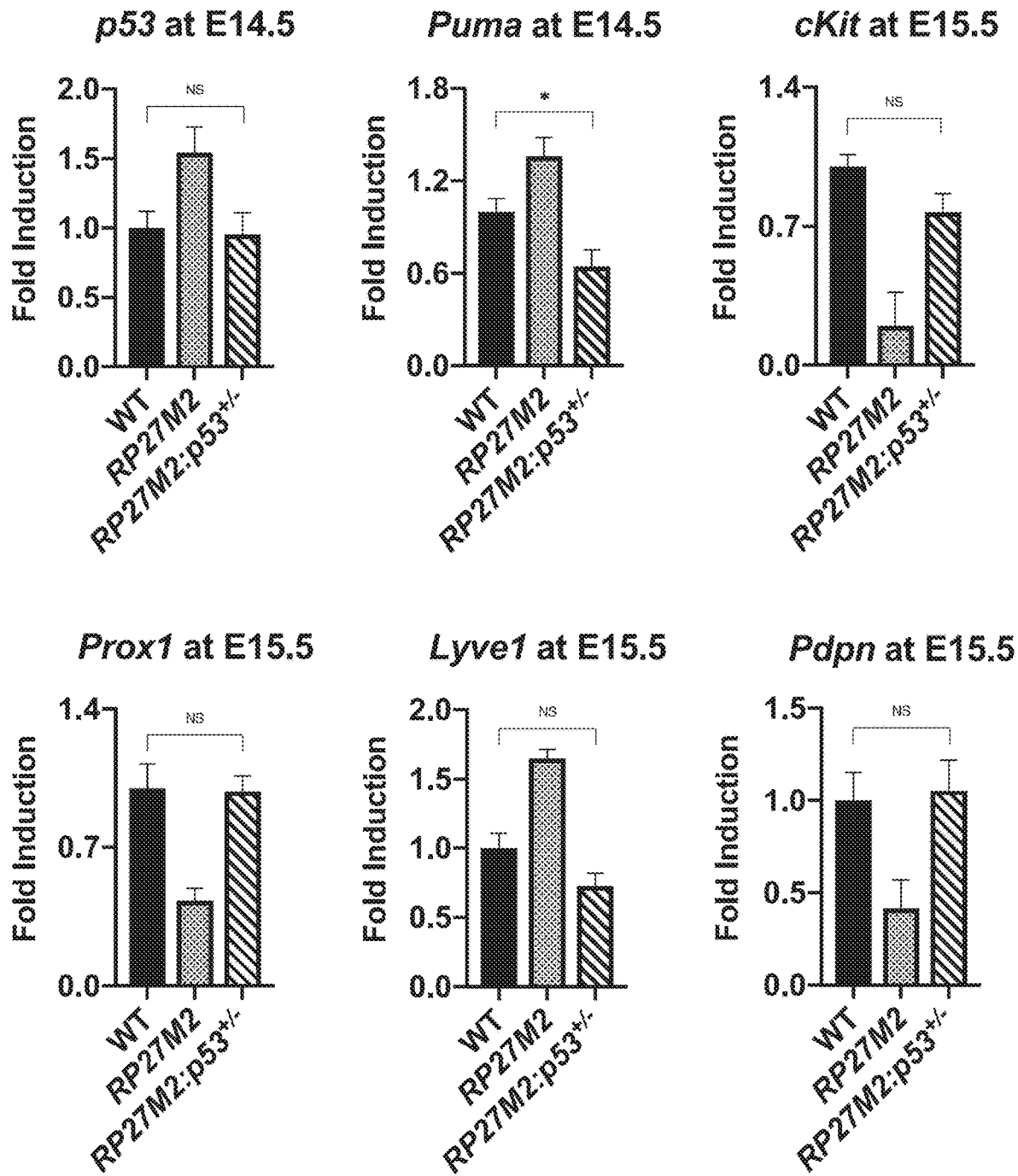
FIGS. 16A and 16B show results from gene expression assays by qPCR (mean+SEM) in RP27M2 (FIG. 16A) and RP27M4 (FIG. 16B) skin with deletion of one copy of p53. Statistical significance determined by t test. NS (not significant), *p<0.05, p<0.01, and *p<0.001.
Figure 16B:
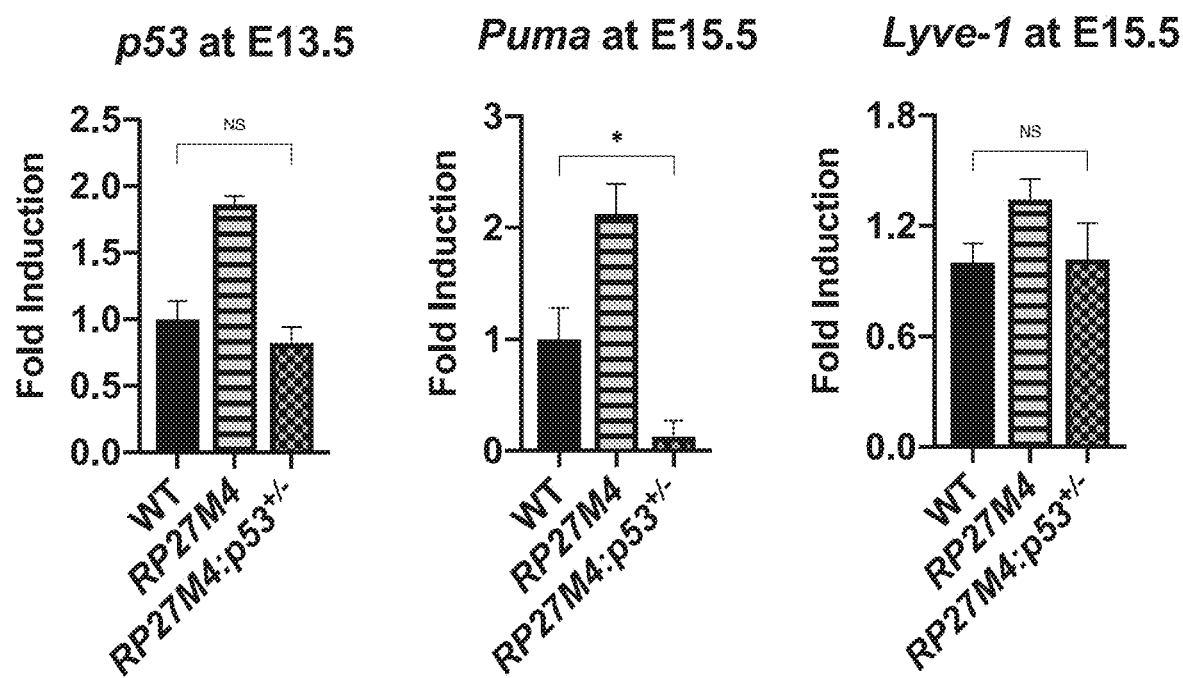

To determine if the lymphatic anomalies were driven by p53, we deleted a single allele of p53 in both models. For this, we crossed Rpl27a$^{low/+}$ animals to mice lacking Mdm2 and p53 (Mdm2$^{-/-}$:p53$^{-/-}$ mice) or Mdm4 and p53 (Mdm4$^{-/-}$:p53$^{-/-}$ mice) to obtain 50% Rpl27a$^{low/+}$:Mdm2$^{+/-}$:p53$^{+/-}$ (RP27M2:p53$^{+/-}$, mice) and 50% Rpl27a$^{low/+}$:Mdm4$^{+/-}$:p53$^{+/-}$ (RP27M4:p53$^{+/-}$) mice respectively. Both crosses resulted in the expected 1:1 Mendelian ratio of progeny (FIG. 8 Panel a) that lived to more than 9 months with no overt pathologies, edema or hemorrhaging (FIG. 8 Panels b-c). Moreover, Lyve-1 staining of RP27M2:p53$^{+/-}$, and RP27M4:p53$^{+/-}$, skin demonstrated that the lymphatics reverted to normal and were similar in size to those in the WT skin (FIG. 8 Panel c). Molecular examination of RP27M2:p53$^{+/-}$, skin indicated that p53, Puma, and c-Kit normalized to WT levels, as did the lymphatic markers Prox-1, Lyve-1, and PdPn (FIGS. 16A and 16B). This normalization of gene expression was also seen in RP27M4:p53$^{+/-}$ skin. Consistent with these data, the distribution of Population III Lyve-1 frequency returned to a level equivalent to the WT distribution (FIG. 10B Panel d). This data showed that gene deletion of one p53 copy reversed hemorrhaging, edema and embryonic lethality in RP27M2 and RP27M4 mice. Taken together, the aberrant lymphatic development in the mutants was p53-dependent, indicating that p53 levels must be kept in check for normal lymphangiogenesis.

Example 8—Chemical Modulation of p53 of Mutant Mice

To confirm the contribution of p53 overexpression to lymphedema, a pharmacological approach was used by testing a known reversible p53 negative modulator, Pifithrin-α (PFT). For this, time mating of Rpl27$^{low/+}$ mice was set up with Mdm2$^{+/-}$, or Mdm4$^{+/-}$, mice. Females carrying both models were injected intraperitoneally (IP) daily from E11.5 to E17.5 and their weight gain was recorded until delivery. Amazingly, pups from both groups were born at a Mendelian ratio with no signs of hemorrhaging (FIG. 9A Panels a-b). PFT-RP27M2 mice were indistinguishable from WT and 100% survived until at least 10 days old (FIG. 9A Panel a and data not shown). However, PFT-RP27M4 pups had an overall edema that was considerably reduced, a slightly looser skin, and excess skin in the area around the neck (FIG. 9A Panel a). H&E staining of dorsal skin indicated that the skin looked normal in both mutants with no evident subcutaneous edema (FIG. 9B Panel b). 100% of PFT-RP27M4 mice died did shortly after birth. Lyve-1 staining of PFT-treated RP27M2 and RP27M4 skin at postnatal day 0 (P0) showed that lymphatic vessels reverted to a normal size (FIG. 9B Panel c). It was speculated that the extent of phenotypic rescue at the low PFT dose used may be determined by the severity of the presentation. Therefore, increasing the amount of PFT given to the RP27M4 carrying mothers may allow for RP27M4 pups to survive.

In conclusion, based on examples 7 and 8, genetic inhibition by single allele loss of p53 or drug-driven control of p53, reversed cutaneous lymphatic defects, hemorrhaging, edema and embryonic lethality. These results demonstrate that elevated p53 contributes to lymphatic defects. The data also indicate that pharmacological modulation of p53 in mid-to-late gestation is clinically pertinent to treatment of lymphedema where p53 is overexpressed in lymphatic endothelium.

Example 9—p53 Overexpression in Lymphatic Defects and not in Normal Lymphatics

To test for the involvement of p53 overexpression in cases of human lymphedema, p53 levels were checked by immunostaining in eight lymphatic diseases associated with severe edema. High p53 positivity was observed in the lymphatic endothelium in six out of eight samples. Interestingly, venous and arterial endothelium were negative in the same p53-positive patient tissues (FIG. 11, FIG. 12 Panel a). Staining for p53 in the endothelial cells of normal neonatal and adult human skin was also negative (FIGS. 11, FIG. 12 Panels a-b). In lymphatic diseases, more often females are affected than males (National Organization of Rare Diseases). Therefore, gender differences were checked in the disease presentation of the mutants. Based on edema and hemorrhage scoring following defined criteria (FIG. 14A Panel a), it was noted that at E15.5, RP27M2 females were on average two-fold more significantly affected by both hemorrhaging and edema than males, while RP27M4 females suffered from more severe hemorrhaging than males with a tendency for worsening of edema (FIG. 17 Panel a). Sex differences for edema in RP27M4 mice were likely masked by the extensive magnitude of this phenotype in the mutants. Taken together, p53 upregulation plays a central role lymphatic defects and the murine models seem like a good representative model of human lymphatic defects.

Example 10—Discussion

For the first time in these studies, a link was shown between the transcription factor p53 and the lymphatic system. The characterization of two mouse models of high p53 demonstrated that p53 overexpression leads to lymphatic defects, in particular lymphedema, during embryonic development. As such, RP27M2 and RP27M4 mice that express elevated p53 triggered by ribosomal stress display pronounced cutaneous edema and hemorrhaging during late gestation. These mice also exhibit reduced cutaneous lymphatic vasculature that becomes enlarged and filled with blood, and a stark delay in formation of mesenteric lymphatics.

The lymphatic phenotypes in the mutants were first observed at E14.5 (FIG. 2, FIG. 14B Panels b-c), coinciding with the onset of the lymphatic proliferation that establishes the lymphatic network throughout the body. Lymphatic structures continue to develop in the edemic embryos but with a clear delay compared to WT mice, likely due to the considerable drop in Prox-1 and its target Vegfr-3 in these tissues as seen in other lymphedema mice (FIGS. 16A and 16B). Interestingly, a huge decline was observed in c-Kit expression in both mutants. Stanczuk L. et al. also noticed a reduction of c-Kit in mice heterozygous for Vegfr-3 and p110α, the catalytic subunit of PI3K, a key downstream effector of Vegfr signaling in endothelial cells. A part of the lymphatic vasculature of the mesentery in these mice developed from a non-venous c-Kit lineage cells of hemogenic endothelial origin, which is contrary to the long held doctrine that mammalian lymphatic vessels sprout from veins. Therefore, the depletion of c-Kit in the mutants may suggest that c-Kit+ hematopoietic progenitors may contribute to the genesis of skin lymphatic vessels. Further investigation into the origins of dermal lymphatic vessels is ongoing and is a prerequisite for restoring function in diseases with lymphatic deficiencies.

In agreement with the confocal microscopy of E14.5 and E16.5 skin that showed a reduced blood vessel density, FACS sorting of E15.5 panendothelial dermal cells (CD31$^+$:CD45$^-$) revealed a considerable decrease in BECs (Population II) in the mutants. However, the drastic changes in the LEC subpopulations and the timing of lymphatic anomalies in the high p53 models suggests that the lymphatic system is more sensitive to the deleterious effects of p53 overexpression than the blood network. This sensitivity exposed an inability to properly drain lymph, which resulted in engorged lymphatics, hemorrhaging and generalized edema. The compensatory response of increasing subpopulation IIIB of LECs, the putative collector lymphatics, appears to have ultimately failed when faced with the large volumes of blood mixed interstitial fluid. Analyzing the transcriptional profiles of the 4 endothelial clusters is important as it may lead to the further identification of these cell populations, particularly Population I that was consider as potential progenitor cells that appear to be accumulating in the mutants. This approach may also reveal additional diagnostic markers of lymphatic disease and ultimately unveil how p53 orchestrates lymphatic disorders.

Mouse models of high p53 typically show p53-induced Caspase-dependent apoptosis in affected tissues. Despite an overexpression of Puma and Noxa mRNA in the mutants (FIG. 15 Panel a and data not shown), surprisingly Caspase-3 was not detected (data not shown). This observation does not preclude a Caspase-independent cell death, but the increase in cell cycle arrest due to p21 upregulation (FIG. 5 Panel e) points to a preferential mode of action of p53 in the lymphatic system. p53 overexpression was shown to induce a p21-dependent cell cycle arrest in mutant lymphatic endothelium (FIG. 5 Panel e), resulting in an insufficiency of lymphatic networking. Hence, the inability to efficiently drain the lymph from the interstitial tissues led to extreme cutaneous edema and vessel leakage in the mutants (FIG. 2 Panel c). The phenotypic concordance of both models and the near complete penetrance of their manifestations strengthens the conclusion that wild type p53 is the common culprit of these manifestations.

Abnormalities associated with the loss of Mdm4 were observed to be much more accentuated than those with loss of Mdm2 (FIG. 2c), which is the reverse of what is seen with Mdm2 and Mdm4 gene deletion models. Mdm2, the main p53 inhibitor, is an E3 ubiquitin ligase that degrades p53, while Mdm4 does not. Therefore, Mdm2 generally exerts a more powerful control on p53 stability and activity than its family member Mdm4; thus lack of Mdm2 typically affects health much more seriously than Mdm4 loss. The increased severity of Mdm4 associated lymphedema and hemorrhaging may be due to intensified p53 expression at E13.5 in RP27M4 skin, a day earlier than in RP27M2 mice (FIG. 15 Panel a). Remarkably, Mdm2 levels in RP27M4 skin were low compared to WT skin, which may have (without wishing to be limited by any one theory) further disrupted the negative regulation by Mdm4 and its interaction with Mdm2 to efficiently downregulate p53. Without wishing to be limited by theory, an alternate explanation for this unexpected observation is a potential additive contribution of p53-independent functions of Mdm4 to the severity of the lymphatic anomalies. Nevertheless, both models support a relationship between p53 activation and lymphatic defects, largely through impeding proliferation via growth arrest.

Hirashima et al. (2008) identified the Apoptosis Stimulating Protein of p53 (Aspp1) as an endothelial-specific gene functioning during mouse embryonic development. Aspp1-null embryos exhibited an impaired cutaneous lymphatic drainage and edema that resolved in adulthood, suggesting that Aspp1, a promoter of the apoptotic activity of p53, plays a role a lymphangiogenesis. However, the function of Aspp1 in this system seems to be entirely p53-independent. In contrast, the phenotypes of the mutants are completely p53-dependent. Genetic deletion of one copy of p53 in both RP27M2 and RP27M4 mice reversed symptomatic lymphedema and hemorrhaging. RP27M2:p53$^{+/-}$ and RP27M4:p53$^{+/-}$ were born at a Mendelian ratio and lived normally with no overt pathologies (FIG. 8). Expression of p53 targets, lymphatic markers, and the ratios of FACS-sorted CD45-:CD31+ cells in RP27M2:p53$^{+/-}$ and RP27M4:p53$^{+/-}$ mice were restored comparable to WT levels (FIGS. 16A and 16B).

More importantly, pharmacologic control of p53 levels in both mutants successfully reversed symptoms of edema and hemorrhaging and mice were born following a Mendelian ratio. However, RP27M4 mice were born with a loose skin around their neck and did not survive past the first day perhaps since RP27M4 phenotypes were much more severe than those of RP27M2 mice. Starting PFT injections a day early or testing an increased range of PFT, c-PFT, PFT-μ, PK11000 and ReACp53 may replicate the same results gained from treated RP27M2 mice. Nevertheless, attaining a symptomatic reversal in a genetic model of lymphedema with pharmacological means has not yet been established and the outcomes with PFT treatment appear in this context extraordinary and very promising for future translational research.

The findings were further corroborated in lymphedema-associated lymphatic disorders. p53 was detected at high levels specifically in the lymphatic endothelium and not in the venous or arterial endothelium of the same patient skin. From 8 cases, 6 disease tissue tested positive for p53, while normal neonatal and adult skin were negative for p53 in any endothelial tissue (FIGS. 11 and 12). This observation once again corroborated findings from the mutants that show a striking resemblance to multiple mouse models of lymphedema and human lymphatic disease. Of note, Rpl27$^{low/+}$ embryos had some low level of cutaneous hemorrhaging and edema along with less dense lymphatics. Therefore, the contribution of ribosomal stress to the pathogenesis of lymphatic defects cannot be entirely excluded. Coincidently, hydrops fetalis associated with the inherited Diamond- Blackfan anemia disorder (DBA) was highly linked to mutations in genes coding for ribosomal proteins. A subsequent p53 stabilization triggered by ribosomal stress was detected and a role for p53 in the pathogenesis of DBA was demonstrated suggesting that p53 is the common factor in lymphatic malformations associated with hydrops fetalis or lymphedema. Keeping p53 at bay is then imperative for the proper formation of the lymphatic network. After all, having no p53, as in p53-null mice, in general did not affect gestation.

This study, the first to highlight a role of p53 in lymphatic disease, indicates that the lymphatic system is particularly sensitive to high levels of p53 and that p53 overexpression in a subpopulation of endothelial cells disrupts the proper progression of lymphangiogenesis. Therefore, while p53 is not required for normal formation, p53 needs to remain restricted during development to circumvent its immediate response when p53 passes a certain threshold of cellular stressors. p53 would then trigger its typical anti-proliferative effects that promote symptomatic lymphedema.

While multiple embodiments are disclosed, still other embodiments of the present disclosure will become apparent to those skilled in the art from the following detailed description. As will be apparent, the disclosed compositions and methods are capable of modifications in various obvious aspects, all without departing from the present spirit and scope of the disclosure. Accordingly, the detailed description is to be regarded as illustrative in nature and not restrictive.

All references disclosed herein, whether patent or non-patent, are hereby incorporated by reference as if each was included at its citation, in its entirety. In case of conflict between reference and specification, the present specification, including definitions, will control.

We claim:

1. A method of treating a subject at risk for developing a disease or condition associated with lymphatic vasculature, the method comprising:
   reducing activity of p53 in a subject at risk for or suffering from a disease or condition associated with lymphatic vasculature.

2. The method of claim 1, wherein the disease or condition is lymphedema.

3. The method of claim 2, wherein the disease or condition is selected from Milroy's disease, Klippel-Trenaunay and Cloves Syndromes.

4. The method of claim 3, wherein the reducing involves administering a compound or pharmaceutically acceptable salt thereof to the subject.

5. The method of claim 4, wherein the compound or pharmaceutically acceptable salt thereof is an anti-p53 compound.

6. The method of claim 5, wherein the compound is one or more of 2-[2-Imino-4,5,6,7-tetrahydrobenzothiazol-3-yl]-1-p-tolylethanone, and Cyclic Pifithrin-α hydrobromide.

7. The method of claim 6, wherein the administering is systemic.

8. The method of claim 7, wherein the administering is intravenous injection or infusion.

9. The method of claim 8, wherein the subject is a human subject.

10. The method of claim 9, wherein the human subject is an adult subject.

11. A method of promoting development of a lymphatic vessel in a subject in need thereof, the method comprising:
    reducing activity of p53 in, at, or near a lymphatic vessel cell.

12. The method of claim 11, wherein the subject is at risk for developing, or suffers from lymphedema.

13. The method of claim 12, wherein the lymphedema is associated with Milroy's disease, Klippel-Trenaunay Syndrome, and Cloves Syndrome.

14. The method of claim 13, wherein the reducing involves administering a compound or pharmaceutically acceptable salt thereof to the subject.

15. The method of claim 14, wherein the compound or pharmaceutically acceptable salt thereof is one or more of 2-[2-Imino-4,5,6,7-tetrahydrobenzothiazol-3-yl]-1-p-tolylethanone, and cyclic-pifithrin.

16. The method claim 15, wherein the administering is intravenous injection or infusion.

17. The method of claim 16, wherein the subject is a human subject.

18. The method of claim 17, wherein the human subject is an adult subject.

* * * * *